(12) United States Patent
Fontayne et al.

(10) Patent No.: US 11,091,552 B2
(45) Date of Patent: Aug. 17, 2021

(54) SPECIFIC BINDING MOLECULE DIRECTED AGAINST GALECTIN-3 PROTEIN

(71) Applicants: LABORATOIRE FRANCAIS DU FRACTIONNEMENT ET DES BIOTECHNOLOGIES, Les Ulis (FR); CENTRE NATIONAL DE LA RECHERCHE SCIENTIFIQUE, Paris (FR); UNIVERSITE DE BORDEAUX, Bordeaux (FR)

(72) Inventors: Alexandre Fontayne, La Madeleine (FR); Philippe Mondon, Neuve Chapelle (FR); Jeanny Laroche-Traineau, Saint Aubin de Médoc (FR); Marie-Josée Jacobin-Valat, Saint Morillon (FR); Martine Cérutti, Saint Christol les Ales (FR); Gisèle Clofent-Sanchez, Le Pian Médoc (FR); Cyril Lorenzato, Bourdeaux (FR); Audrey Hémadou, Pau (FR)

(73) Assignees: LABORATOIRE FRANAIS DU FRACTIONNEMENT ET DES BIOTECHNOLOGIES, Les Ulis (FR); CENTRE NATIONAL DE LA RECHERCHE SCIENTIFIQUE, Paris (FR); UNIVERSITE DE BORDEAUX, Bordeaux (FR)

(*) Notice: Subject to any disclaimer, the term of this patent is extended or adjusted under 35 U.S.C. 154(b) by 0 days.

(21) Appl. No.: 16/753,671

(22) PCT Filed: Oct. 5, 2018

(86) PCT No.: PCT/EP2018/077131
§ 371 (c)(1),
(2) Date: Apr. 3, 2020

(87) PCT Pub. No.: WO2019/068863
PCT Pub. Date: Apr. 11, 2019

(65) Prior Publication Data
US 2021/0079101 A1 Mar. 18, 2021

(30) Foreign Application Priority Data

Oct. 5, 2018 (EP) .................................... 17306337

(51) Int. Cl.
*C07K 16/00* (2006.01)
*A61P 9/10* (2006.01)
(Continued)

(52) U.S. Cl.
CPC ............ *C07K 16/2851* (2013.01); *A61P 9/10* (2018.01); *A61K 2039/505* (2013.01);
(Continued)

(58) Field of Classification Search
None
See application file for complete search history.

(56) References Cited

U.S. PATENT DOCUMENTS

2010/0143954 A1   6/2010   Muntendam

FOREIGN PATENT DOCUMENTS

WO   2008112559 A1   9/2008
WO   2016004093 A2   1/2016

OTHER PUBLICATIONS

Altschul et al., "Basic Local Alignment Search Tool.," J. Mol. Biol, vol. 215, pp. 403-410, May 15, 1990.
(Continued)

*Primary Examiner* — Aurora M Fontainhas
(74) *Attorney, Agent, or Firm* — Greer, Burns & Crain, Ltd.

(57) ABSTRACT

A specific binding molecule is provided which binds to galectin-3 protein, methods of their production and methods of use.

17 Claims, 7 Drawing Sheets
(7 of 7 Drawing Sheet(s) Filed in Color)

Specification includes a Sequence Listing.

(51) Int. Cl.
*C07K 16/28* (2006.01)
*A61K 39/00* (2006.01)

(52) U.S. Cl.
CPC .... *C07K 2317/55* (2013.01); *C07K 2317/565* (2013.01); *C07K 2317/622* (2013.01)

(56) References Cited

OTHER PUBLICATIONS

Karlin et al., "Methods for Assessing the Statistical Significance of Molecular Sequence Features by Using General Scoring Schemes.," Proc. Natl. Acad. Sci. USA, vol. 87, pp. 2264-2268, Mar. 1990.
Karlin et al., "Applications and Statistics for Multiple High-Scoring Segments in Molecular Sequences.," Proc. Natl. Acad. Sci. USA, vol. 90, pp. 5873-5877, Jun. 1993.
Deramchia et al., "In Vivo Phage Display to Identify New Human Antibody Fragments Homing to Atherosclerotic Endothelial and Subendothelial Tissues.," The American Journal of Pathology, vol. 180, No. 6, pp. 2576-2589, Jun. 2012.
Fashanu et al., "Galectin-3 and Venous Thromboembolism Incidence: The Atherosclerosis Risk in Communities (ARIC) Study.," pp. 223-230, Jul. 21, 2017.
Felgner et al., "Cationic Liposome-Mediated Transfection.," Nature, vol. 337, pp. 387-388, Jan. 26, 1989.
Hemadou et al., "An Innovative Flow Cytometry Method to Screen Humans scFv-phages Selected by in Vivo Phage-display in an Animal Model of Atherosclerosis.," Scientific Reports, Oct. 9, 2018.
Nachtigal et al., "Galectin-2 Gene Inactivation Reduces Atherosclerotic Lesions and Adventitial Inflammation in ApoE-Deficient Mince.," The American Journal of Pathology, vol. 172, pp. 247-255, Jan. 2008.
Rice et al., "EMBOSS: The European Molecular Biology Open Software Suite.," Trends in Genetics, vol. 16, No. 6, pp. 276-277, Jun. 2000.
Takemoto et al, "Galectin-3 Regulates Atrial Fibrillation Remodeling and Predicts Catheter Ablation Outcomes.," JACC: Basic to Translational Science vol. 1 No. 3, pp. 143-154, Apr. 2016.
European Search Report from EP Patent Application No. 17306337, dated Nov. 20, 2017.

SEQUENCE LISTING

```
<160> NUMBER OF SEQ ID NOS: 43

<210> SEQ ID NO 1
<211> LENGTH: 120
<212> TYPE: PRT
<213> ORGANISM: Artificial Sequence
<220> FEATURE:
<223> OTHER INFORMATION: Synthetized - VH / specific binding molecule

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Phe Gly Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Gly Ser Thr Tyr Phe Asp Tyr Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthesized - VL / specific binding molecule

<400> SEQUENCE: 2

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Ser
            20                  25                  30
```

```
Leu Ala Trp Phe Gln Gln Arg Pro Gly Glu Ala Pro Asn Leu Leu Ile
            35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Thr Tyr Ser Ala Pro Pro
                85                  90                  95

Thr Phe Gly Gly Gly Thr Lys Leu Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthesized - VH / CDR1

<400> SEQUENCE: 3

Gly Asp Ser Val Ser Ser Asn Asn Phe Gly
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthesized - VH / CDR2

<400> SEQUENCE: 4

Thr Tyr Tyr Arg Ser Lys Trp Tyr Asn
1               5

<210> SEQ ID NO 5
<211> LENGTH: 10
<212> TYPE: PRT
<213> ORGANISM: Artificial Sequence
<220> FEATURE:
<223> OTHER INFORMATION: Synthesized - VH / CDR3

<400> SEQUENCE: 5

Ala Arg Gln Gly Ser Thr Tyr Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Synthesized - VL / CDR1

<400> SEQUENCE: 6

Gln Thr Ile Ser Ser Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Synthesized - VL / CDR2

<400> SEQUENCE: 7

Ser Ala Ser Ser
```

```
<210> SEQ ID NO 8
<211> LENGTH: 9
<212> TYPE: PRT
<213> ORGANISM: Artificial Sequence
<220> FEATURE:
<223> OTHER INFORMATION: Synthesized - VL / CDR3

<400> SEQUENCE: 8

Gln Gln Thr Tyr Ser Ala Pro Pro Thr
1               5

<210> SEQ ID NO 9
<211> LENGTH: 18
<212> TYPE: PRT
<213> ORGANISM: Artificial Sequence
<220> FEATURE:
<223> OTHER INFORMATION: Synthesized - Peptide linker

<400> SEQUENCE: 9

Glu Phe Gly Gly Gly Gly Ser Gly Gly Gly Gly Ser Gly Gly Gly Gly
1               5                   10                  15

Ser Arg

<210> SEQ ID NO 10
<211> LENGTH: 245
<212> TYPE: PRT
<213> ORGANISM: Artificial Sequence
<220> FEATURE:
<223> OTHER INFORMATION: Synthesized - Amino acid sequence of specific
      binding molecule

<400> SEQUENCE: 10

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Phe Gly Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Gly Ser Thr Tyr Phe Asp Tyr Trp Gly Gln
            100                 105                 110

Gly Thr Leu Val Thr Val Ser Ser Glu Phe Gly Gly Gly Gly Ser Gly
        115                 120                 125

Gly Gly Gly Ser Gly Gly Gly Gly Ser Arg Asp Ile Val Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Thr Ile Ser Ser Ser Leu Ala Trp Phe Gln Gln
                165                 170                 175

Arg Pro Gly Glu Ala Pro Asn Leu Leu Ile Tyr Ser Ala Ser Ser Leu
            180                 185                 190

Gln Ser Gly Val Pro Ser Arg Phe Ser Gly Ser Gly Ser Gly Thr Asp
        195                 200                 205
```

```
Phe Thr Leu Thr Ile Ser Ser Leu Gln Pro Glu Asp Phe Ala Thr Tyr
    210                 215                 220
Ser Cys Gln Gln Thr Tyr Ser Ala Pro Pro Thr Phe Gly Gly Gly Thr
225                 230                 235                 240
Lys Leu Glu Ile Lys
            245

<210> SEQ ID NO 11
<211> LENGTH: 737
<212> TYPE: DNA
<213> ORGANISM: Artificial Sequence
<220> FEATURE:
<223> OTHER INFORMATION: Synthesized - Nucleic acid sequence of specific
      binding molecule

<400> SEQUENCE: 11
caggtacagc tgcagcagtc aggtccagga ctggtgaagc cctcgcagac cctctcactc      60
acctgtgcca tctccgggga cagtgtctct agcaacaatt tggttggaa ctggatcagg     120 cagtccccat cgagaggcct tgagtggctg ggaaggacat actacaggtc aagtggtat     180 aatgattatg cagtatctgt gagaagtcga ataaccatca cccagacac atccaagaac     240 cagttctccc tgcagctgaa ctctgtgact cccgaggaca cggccgtgta ttactgtgca     300
agacagggca gcacttactt cgactattgg ggccagggca ccctggtcac tgtctcctca     360
gaattcggtg gcggtggctc gggcggtggt gggtctggtg gcggcggttc tagagacatc     420
gtgatgaccc agtctccatc ctccctgtct gcatctgtag agacagagt caccatcact     480 tgccgggcaa gtcagaccat tagcagctct ttagcttggt ttcagcagag accgggagaa     540
gcccctaacc tcctgatcta tagtgcatcc agtttgcaaa gtggggtccc atcaaggttc     600
agtggcagtg gatctgggac agatttcact ctcaccatca gcagtcttca acctgaagat     660
tttgcaactt actcctgtca acagacttac agtgcccctc ccactttcgg cggagggacc     720
aagctggaga tcaaagt                                                   737

<210> SEQ ID NO 12
<211> LENGTH: 227
<212> TYPE: PRT
<213> ORGANISM: Artificial Sequence
<220> FEATURE:
<223> OTHER INFORMATION: Synthesized - Fc fragment of IgG1

<400> SEQUENCE: 12

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
```

```
            115                 120                 125
Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 477
<212> TYPE: PRT
<213> ORGANISM: Artificial Sequence
<220> FEATURE:
<223> OTHER INFORMATION: Synthesized - Amino acid sequence of fusion
      protein

<400> SEQUENCE: 13

Gly Ser Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Asn Asn Phe Gly Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Val Ser Val Arg Ser Arg Ile Thr Ile Asn Pro Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Gln Gly Ser Thr Tyr Phe Asp Tyr Trp
            100                 105                 110

Gly Gln Gly Thr Leu Val Thr Val Ser Ser Glu Phe Gly Gly Gly Gly
        115                 120                 125

Ser Gly Gly Gly Gly Ser Gly Gly Gly Gly Ser Arg Asp Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Thr Ile Ser Ser Ser Leu Ala Trp Phe
                165                 170                 175

Gln Gln Arg Pro Gly Glu Ala Pro Asn Leu Leu Ile Tyr Ser Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Ser Cys Gln Gln Thr Tyr Ser Ala Pro Pro Thr Phe Gly Gly
225                 230                 235                 240
```

Gly Thr Lys Leu Glu Ile Lys Ala Ala Ala Asp Lys Thr His Thr Cys
            245                 250                 255

Pro Pro Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 14
<211> LENGTH: 1447
<212> TYPE: DNA
<213> ORGANISM: Artificial Sequence
<220> FEATURE:
<223> OTHER INFORMATION: Synthesized - Nucleic acid sequence of fusion
      protein

<400> SEQUENCE: 14
cgccaacgcc ggatcccagg tgcagctgca gcagtctgga cccggcctcg tgaagcctag     60
ccagaccctg tctctgacct gcgccatcag cggcgatagc gtgtccagca acaacttcgg    120
ctggaactgg atcagacaga gcccccagca aggcctggaa tggctgggcc ggacctacta    180
ccggtccaag tggtacaacg actacgccgt gtccgtgcgg agccggatca ccatcaaccc    240
cgacaccagc aagaaccagt tctccctgca gctgaacagc gtgaccccgc aggataccgc    300
cgtgtactac tgtgccagac agggcagcac ctacttcgac tactgggccc agggcaccct    360
cgtgaccgtg tctagcgaat tggcggcgg aggatctggc ggaggcggaa gtggcggagg    420
gggctctaga gacatcgtga tgacccagag ccccctccag ctgtctgcca gcgtgggcga    480
cagagtgacc atcacctgta gggccagcca gaccatcagc agcagcctgg cctggtttca    540
gcagcggcca ggcgaagccc ccaacctgct gatctacagc gcctctagcc tgcagagcgg    600 cgtgccagc agattttctg gcagcggctc cggcaccgac ttcaccctga caattagcag    660
cctgcagccc gaggacttcg ccacctacag ctgccagcag acctactccg cccctcctac    720

```
atttggaggc ggcaccaagc tggaaatcaa ggcggccgcg gacaaaactc acacatgccc      780
accgtgccca gcacctgaac tcctgggggg accgtcagtc ttcctcttcc ccccaaaacc      840
caaggacacc ctcatgatct cccggacccc tgaggtcaca tgcgtggtgg tggacgtgag      900
ccacgaagac cctgaggtca agttcaactg gtacgtggac ggcgtggagg tgcataatgc      960
caagacaaag ccgcgggagg agcagtacaa cagcacgtac cgtgtggtca gcgtcctcac     1020
cgtcctgcac caggactggc tgaatggcaa ggagtacaag tgcaaggtct ccaacaaagc     1080
cctcccagcc cccatcgaga aaaccatctc caaagccaaa gggcagcccc gagaaccaca     1140
ggtgtacacc ctgcccccat cccgggatga gctgaccaag aaccaggtca gcctgacctg     1200
cctggtcaaa ggcttctatc ccagcgacat cgccgtggag tgggagagca atgggcagcc     1260
ggagaacaac tacaagacca cgcctcccgt gctggactcc gacggctcct tcttcctcta     1320
tagcaagctc accgtggaca agagcaggtg gcagcagggg aacgtcttct catgctccgt     1380
gatgcatgag gctctgcaca accactacac gcagaagagc ctctccctgt ctccgggtaa     1440
atgatga                                                              1447
```

<210> SEQ ID NO 15
<211> LENGTH: 6
<212> TYPE: PRT
<213> ORGANISM: Artificial Sequence
<220> FEATURE:
<223> OTHER INFORMATION: Synthesized - Suitable peptide tag

<400> SEQUENCE: 15

His His His His His His
1               5

<210> SEQ ID NO 16
<211> LENGTH: 12
<212> TYPE: PRT
<213> ORGANISM: Artificial Sequence
<220> FEATURE:
<223> OTHER INFORMATION: Synthesized - Suitable peptide tag

<400> SEQUENCE: 16

Glu Asp Gln Val Asp Pro Arg Leu Ile Asp Gly Lys
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthesized - Suitable peptide tag

<400> SEQUENCE: 17

Trp Ser His Pro Gln Phe Glu Lys
1               5

<210> SEQ ID NO 18
<211> LENGTH: 14
<212> TYPE: PRT
<213> ORGANISM: Artificial Sequence
<220> FEATURE:
<223> OTHER INFORMATION: Synthesized - Suitable peptide tag

<400> SEQUENCE: 18

Gly Lys Pro Ile Pro Asn Pro Leu Leu Gly Leu Asp Ser Thr
1               5                   10

```
<210> SEQ ID NO 19
<211> LENGTH: 9
<212> TYPE: PRT
<213> ORGANISM: Artificial Sequence
<220> FEATURE:
<223> OTHER INFORMATION: Synthesized - Suitable peptide tag

<400> SEQUENCE: 19

Ile Pro Asn Pro Leu Leu Gly Leu Asp
1               5

<210> SEQ ID NO 20
<211> LENGTH: 10
<212> TYPE: PRT
<213> ORGANISM: Artificial Sequence
<220> FEATURE:
<223> OTHER INFORMATION: Synthesized - Suitable peptide tag

<400> SEQUENCE: 20

Glu Gln Lys Leu Ile Ser Glu Glu Asp Leu
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthesized - Suitable peptide tag

<400> SEQUENCE: 21

Gly Gly Gly Gly Ser Leu Pro Glu Thr Gly Gly Ala Ala
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthesized - Suitable peptide tag

<400> SEQUENCE: 22

Gly Gly Gly Gly Ser Cys Cys Ala Ala
1               5

<210> SEQ ID NO 23
<211> LENGTH: 18
<212> TYPE: PRT
<213> ORGANISM: Artificial Sequence
<220> FEATURE:
<223> OTHER INFORMATION: Synthesized - Suitable peptide tag

<400> SEQUENCE: 23

Pro Thr Leu Tyr Asn Val Ser Leu Val Met Ser Asp Thr Ala Gly Thr
1               5                   10                  15

Cys Tyr

<210> SEQ ID NO 24
<211> LENGTH: 42
<212> TYPE: DNA
<213> ORGANISM: Artificial Sequence
<220> FEATURE:
<223> OTHER INFORMATION: Synthesized - Suitable peptide spacer

<400> SEQUENCE: 24
ggtggcggtg gctcgggcgg tggtgggtct ggtggcggcg gt                              42
```

```
<210> SEQ ID NO 25
<211> LENGTH: 51
<212> TYPE: DNA
<213> ORGANISM: Artificial Sequence
<220> FEATURE:
<223> OTHER INFORMATION: Synthesized PCR primer for P3/A-VH

<400> SEQUENCE: 25
gctacttaag ggtgtccagt gccaggtgca gctgcagcag tctggacccg g           51

<210> SEQ ID NO 26
<211> LENGTH: 35
<212> TYPE: DNA
<213> ORGANISM: Artificial Sequence
<220> FEATURE:
<223> OTHER INFORMATION: Synthesized PCR primer for P3/A-VL

<400> SEQUENCE: 26
gctacgtacg cttgatttcc agcttggtgc cgcct                             35

<210> SEQ ID NO 27
<211> LENGTH: 109
<212> TYPE: DNA
<213> ORGANISM: Artificial Sequence
<220> FEATURE:
<223> OTHER INFORMATION: Synthesized Primer P1-VH-C3

<400> SEQUENCE: 27
cagaggagag ctagcgaagc ttgccgccac catgcgatgg agctggatct tcctgctgct  60
gctgagcatc accagcgcca acgcccaggt gcagctgcag cagtctgga             109

<210> SEQ ID NO 28
<211> LENGTH: 45
<212> TYPE: DNA
<213> ORGANISM: Artificial Sequence
<220> FEATURE:
<223> OTHER INFORMATION: Synthesized Primer P2-VH-C3

<400> SEQUENCE: 28
gctcgcggcc gcactcaccg ctagacacgg tcacgagggt gccct                  45

<210> SEQ ID NO 29
<211> LENGTH: 107
<212> TYPE: DNA
<213> ORGANISM: Artificial Sequence
<220> FEATURE:
<223> OTHER INFORMATION: Synthesized Primer P1-VL-C3

<400> SEQUENCE: 29
ttccatttca gactagtaag cttgccgcca ccatgcgatg gagctggatc ttcctgctgc  60
tgctgagcat caccagcgcc aacgccgaca tcgtgatgac ccagagc               107

<210> SEQ ID NO 30
<211> LENGTH: 41
<212> TYPE: DNA
<213> ORGANISM: Artificial Sequence
<220> FEATURE:
<223> OTHER INFORMATION: Synthesized Primer P2-VL-C3

<400> SEQUENCE: 30
gccgcaaagt gcacttacgc ttgatttcca gcttggtgcc g                      41

<210> SEQ ID NO 31
<211> LENGTH: 18
```

```
<212> TYPE: DNA
<213> ORGANISM: Artificial Sequence
<220> FEATURE:
<223> OTHER INFORMATION: Synthesized Primer Ch-Int 5'

<400> SEQUENCE: 31
gtgagtgcgg ccgcgagc                                                   18

<210> SEQ ID NO 32
<211> LENGTH: 30
<212> TYPE: DNA
<213> ORGANISM: Artificial Sequence
<220> FEATURE:
<223> OTHER INFORMATION: Synthesized Primer CH-Int 3'

<400> SEQUENCE: 32
gatcctcggc gcgcctcatc atttacccgg                                      30

<210> SEQ ID NO 33
<211> LENGTH: 20
<212> TYPE: DNA
<213> ORGANISM: Artificial Sequence
<220> FEATURE:
<223> OTHER INFORMATION: Synthesized Primer CK-Int 5'

<400> SEQUENCE: 33
gtaagtgcac tttgcggccg                                                 20

<210> SEQ ID NO 34
<211> LENGTH: 43
<212> TYPE: DNA
<213> ORGANISM: Artificial Sequence
<220> FEATURE:
<223> OTHER INFORMATION: Synthesized Primer CKI-XbaI-5'

<400> SEQUENCE: 34
atcagcgagc tctagactat caacactctc ccctgttgaa gct                       43

<210> SEQ ID NO 35
<211> LENGTH: 105
<212> TYPE: DNA
<213> ORGANISM: Artificial Sequence
<220> FEATURE:
<223> OTHER INFORMATION: Synthesized Primer P1-VL-C3-2

<400> SEQUENCE: 35
cagaggagag ctagcaagct tgccgccacc atgcgatgga gctggatctt cctgctgctg     60
ctgagcatca ccagcgccaa cgccgacatc gtgatgaccc agagc                    105

<210> SEQ ID NO 36
<211> LENGTH: 41
<212> TYPE: DNA
<213> ORGANISM: Artificial Sequence
<220> FEATURE:
<223> OTHER INFORMATION: Synthesized Primer P2-VL-C3-2

<400> SEQUENCE: 36
gccgcaaagt gcacttacgc ttgatttcca gcttggtgcc g                         41

<210> SEQ ID NO 37
<211> LENGTH: 109
<212> TYPE: DNA
<213> ORGANISM: Artificial Sequence
<220> FEATURE:
<223> OTHER INFORMATION: Synthesized Primer P1-VH-C3-2
```

<400> SEQUENCE: 37
ccatttcaga ctagtgaagc ttgccgccac catgcgatgg agctggatct tcctgctgct    60
gctgagcatc accagcgcca acgcccaggt gcagctgcag cagtctgga              109

<210> SEQ ID NO 38
<211> LENGTH: 44
<212> TYPE: DNA
<213> ORGANISM: Artificial Sequence
<220> FEATURE:
<223> OTHER INFORMATION: Synthesized Primer P2-VH-C3-2

<400> SEQUENCE: 38
gctcgcggcc gcactcacgc tagacacggt cacgagggtg ccct                   44

<210> SEQ ID NO 39
<211> LENGTH: 46
<212> TYPE: DNA
<213> ORGANISM: Artificial Sequence
<220> FEATURE:
<223> OTHER INFORMATION: Synthesized Primer 3'CH-xba

<400> SEQUENCE: 39
aggctgatca gcgagctcta gatcatcatt tacccggaga caggga                 46

<210> SEQ ID NO 40
<211> LENGTH: 42
<212> TYPE: DNA
<213> ORGANISM: Artificial Sequence
<220> FEATURE:
<223> OTHER INFORMATION: Synthesized Primer 3'CK-asc

<400> SEQUENCE: 40
gatcctcggc gcgccctatc aacactctcc cctgttgaag ct                     42

<210> SEQ ID NO 41
<211> LENGTH: 60
<212> TYPE: DNA
<213> ORGANISM: Artificial Sequence
<220> FEATURE:
<223> OTHER INFORMATION: Synthesized Primer P1-MB7-V4

<400> SEQUENCE: 41
tttcctctcc tgacagctag cgaagcttgc cgccaccatg cgatggagct ggatcttcct  60

<210> SEQ ID NO 42
<211> LENGTH: 39
<212> TYPE: DNA
<213> ORGANISM: Artificial Sequence
<220> FEATURE:
<223> OTHER INFORMATION: Synthesized Primer P2-WT-HI

<400> SEQUENCE: 42
cttgccggcc tcgagtcatc atttacccgg agacaggga                         39

<210> SEQ ID NO 43
<211> LENGTH: 42
<212> TYPE: DNA
<213> ORGANISM: Artificial Sequence
<220> FEATURE:
<223> OTHER INFORMATION: Synthesized Primer P2-WT-KI

<400> SEQUENCE: 43
cttgccggcc tcgagctatc aacactctcc cctgttgaag ct                     42

SPECIFIC BINDING MOLECULE DIRECTED AGAINST GALECTIN-3 PROTEIN

REFERENCE TO AN ELECTRONIC SEQUENCE LISTING

The contents of the electronic sequence listing (17K8400.txt; Size: 22189 bytes was created on Dec. 1, 2020) is herein incorporated by reference in its entirety.

BACKGROUND

The present invention relates to a specific binding molecule which specifically binds to galectin-3 protein, methods of their production and methods of use.

Lectins are proteins that bind to specific carbohydrate structures and can thus recognize particular glycoconjugates. Galectins are a family of over 10 structurally related lectins that bind beta-galactosides. Galectin-3 is a 26 kDa beta-galactoside-binding protein belonging to the galectin family. This protein is composed of a carboxyl-terminal carbohydrate-recognition domain (CRD) and amino-terminal tandem repeats. Galectin-3 is found in epithelia of many organs, as well as in various inflammatory cells, including macrophages, dendritic cells and Kupffer cells. The expression of galectin-3 is upregulated during inflammation, cell proliferation, cell differentiation, and through transactivation by viral proteins. Galectin-3 is involved in cardiac fibrosis, cardiac remodeling, and inflammation. Many studies have shown that galectin-3 may regulate inflammation through a variety of mechanisms. Endogenous galectin-3 has been shown to be involved in the pathogenesis of various inflammatory diseases, such as fibrosis in the lung, liver, and heart, diabetes mellitus, coronary artery disease, and allergic diseases. It is known that Galectin-3 is highly expressed in macrophages within human atherosclerotic plaques.

Atherosclerosis is a chronic and systemic inflammatory disease affects arteries with large and medium caliber. This pathology is characterized by the build-up of lipid-rich plaques within the arterial wall which can evolve into stable or vulnerable atheroma plaques. Stable atheroma tends to be asymptomatic unless expanding atherosclerotic lesions cause severe narrowing of the lumen, one of the consequences being ischemia. Vulnerable atheroma has more dramatic impacts due to the presence of a large lipid core covered with a thin fibrous cap at high risk of rupture and thrombi formation. These events precipitate the clinical conditions of stroke and myocardial infarction. Nowadays, high-grade internal carotid artery stenosis (>70% luminal narrowing) is awaited before proposing endarterectomy to the patients. However, the degree of luminal stenosis is not always effective in identifying high-risk patients and less than 50% occlusion in the arterial bed can lead to dramatic events. Atherosclerosis is the main cause of death in the western world with 19 million deaths per year.

SUMMARY

Hence, there is a need for new, effective forms of for diagnosis or treatment of inflammatory disease, particularly treatments that can provide sustained, controlled therapy by local administration with a low degree of side effects. In order to prevent, treat and diagnose inflammatory disease, and in particular atherosclerosis, the inventors have developed a novel specific binding molecule which specifically binds to galectin-3 protein.

The present invention relates to a specific binding molecule which specifically binds to galectin-3 protein, said specific binding molecule comprising:
- a variable heavy domain (VH) comprising an amino acid sequence having at least 90% identity to SEQ ID No. 1, and
- a variable light domain (VL) comprising an amino acid sequence having at least 90% identity to SEQ ID No. 2.

In particular, the inventors have shown that the specific binding molecule of the invention is able to specifically bind to galectin-3 protein.

As used herein, a "specific binding molecule" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organization of the other member of the pair of molecules. Thus, the members of the pair have the property of specifically binding to each other. Examples of types of specific binding pairs are antigen-antibody, biotin-avidin, hormone-hormone receptor, receptor-ligand, enzyme-substrate. The present invention is generally concerned with antigen-antibody type reactions. The specific binding molecule of the present invention binds with greater affinity to galectin-3 protein than to other molecules, i.e. it binds specifically to galectin-3 protein. Specific binding molecules which bind to galectin-3 protein include anti-galectin-3 protein antibodies and aptamers. Typically, the specific binding molecule binds with an affinity (KD) of approximately less than $10^{-6}$ M, more particularly approximately less than $10^{-7}$ M, or less than $10^{-8}$ M or less than $10^{-9}$ M or even lower.

The term "KD" refers to the dissociation equilibrium constant of a particular scFv antibody-antigen interaction. Typically, the specific binding molecule of the invention binds to its target antigen with a dissociation equilibrium constant (KD) of less than approximately $10^{-6}$ M, more particularly less than approximately $10^{-7}$ M, or less than $10^{-8}$ M or less than $10^{-9}$ M or even lower, for example, as determined using Biacore, which uses surface plasmon resonance (SPR) or as determined using BioLayer Interferometry (BLI) technology in a Octet HTX instrument.

In an advantageous embodiment, the variable heavy domain (VH) of the specific binding molecule comprises an amino acid sequence having at least 90% identity to SEQ ID No. 1. Advantageously, the variable heavy domain (VH) of the specific binding molecule comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 1. In a particular advantageous embodiment, the variable heavy domain (VH) of the specific binding molecule has the amino acid sequence SEQ ID No. 1.

In an advantageous embodiment, the variable light domain (VL) of the specific binding molecule comprises an amino acid sequence having at least 90% identity to SEQ ID No. 2. Advantageously, the variable light domain (VL) of the specific binding molecule comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 2. In a particular advantageous embodiment, the variable light domain (VL) of the specific binding molecule has the amino acid sequence SEQ ID No. 2. "Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences.

While there exists a number of methods to measure identity between two polypeptide or two polynucleotide sequences, methods commonly employed to determine identity are codified in computer programs. Preferred computer programs to determine identity between two sequences include, but are not limited to, EMBOSS (The European Molecular Biology Open Software Suite (2000)—Rice, P. Longden, I. and Bleasby, A., Trends in Genetics 16, (6) pp 276-277), Clustal Omega, Needle.

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm.

In one embodiment, the specific binding molecule can be humanized. Humanization of the specific binding molecule may be desired where the molecule is to be used as a therapeutic agent. In a particular advantageous embodiment, the binding specific molecule is a human binding specific molecule.

In an advantageous embodiment, the specific binding molecule can be an antibody or a fragment thereof. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced.

An antibody is a roughly Y-shaped molecule composed of two different polypeptide chains named "heavy" and "light" chains, an antibody being constituted of two heavy and two light chains linked by disulfide bonds. Each heavy chain is composed of a variable domain ("VH domain") and 3 constant domains ("CH1", "CH2" and "CH3" domains), while each light chain is composed of a variable domain ("VL domain") and a constant domain ("CL domain"). In addition, each variable domain (VH or VL domain) is composed of 4 "framework regions" (FR1, FR2, FR3 and FR4), which display less variability among antibodies and are involved in the formation of beta sheets forming the structural framework of the variable domain, and of 3 hypervariable regions commonly named "complementary determining regions" 1, 2 and 3 (CDR1, CDR2, CDR3), which correspond to 3 loops juxtaposed in the folded variable domain at the edge of each beta sheet. The 3 CDR regions are crucial for determining an antibody or antibody fragment specificity, since they are the part of the variable domain mainly in contact with the antigen, especially the CDR3 region of each chain, which corresponds to the rearranged region of the heavy and light chains and is even more variable and more directly in contact with the specific antigen. Examples of antibodies are the immunoglobulin isotypes (e.g., IgG, IgE, IgM, IgD and IgA) and their isotypic subclasses. Antibodies may be polyclonal or monoclonal. A monoclonal antibody may be referred to herein as "mAb".

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanized antibodies, including any polypeptide comprising an immunoglobulin binding domain, whether natural or wholly or partially synthetic. Chimeric molecules comprising an immunoglobulin binding domain, or equivalent, fused to another polypeptide are therefore included.

The specific binding molecule of the invention can be an antibody, more advantageously a monoclonal antibody.

In one embodiment, the specific binding molecule of the invention is a monoclonal antibody directed to galectin-3 protein, and comprising:
  a variable heavy domain (VH) comprising an amino acid sequence having at least 90% identity to SEQ ID No. 1, and
  a variable light domain (VL) comprising an amino acid sequence having at least 90% identity to SEQ ID No. 2.

In an advantageous embodiment, the variable heavy domain (VH) of the monoclonal antibody comprises an amino acid sequence having at least 90% identity to SEQ ID No. 1. Advantageously, the variable heavy domain (VH) of the monoclonal antibody comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 1. In a particular advantageous embodiment, the variable heavy domain (VH) of the monoclonal antibody has the amino acid sequence SEQ ID No. 1. Suitable variable heavy domain (VH) of the monoclonal antibody is

```
                                              (SEQ ID No. 1)
QVQLQQSGPGLVKPSQTLSLTCAISGDSVSSNNFGWNWIRQSPSRGLEWL
GRTYYRSKWYNDYAVSVRSRITINPDTSKNQFSLQLNSVTPEDTAVYYCA
RQGSTYFDYWGQGTLVTVSS.
```

In an advantageous embodiment, the variable light domain (VL) of the monoclonal antibody comprises an amino acid sequence having at least 90% identity to SEQ ID No. 2. Advantageously, the variable light domain (VL) of the monoclonal antibody comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 2. In a particular advantageous embodiment, the variable light domain (VL) of the monoclonal antibody has the amino acid sequence SEQ ID No. 2.

Suitable variable light domain (VL) of the monoclonal antibody is

```
                                              (SEQ ID No. 2)
DIVMTQSPSSLSASVGDRVTITCRASQTISSSLAWFQQRPGEAPNLLIYS
ASSLQSGVPSRFSGSGSGTDFTLTISSLQPEDFATYSCQQTYSAPPTFGG
GTKLEIK.
```

Advantageously, the monoclonal antibody directed to galectin-3 protein comprises:
- a variable heavy domain (VH) of SEQ ID No. 1, comprising CDR1, CDR2 and CDR3 regions constituted of SEQ ID No. 3, SEQ ID No. 4 and SEQ ID No. 5, and
- a variable light domain (VL) of SEQ ID No. 2, comprising CDR1, CDR2 and CDR3 regions constituted of SEQ ID No. 6, SEQ ID No. 7 and SEQ ID No. 8.

Suitable CDR1 of the variable heavy domain (VH) of the monoclonal antibody is GDSVSSNNFG (SEQ ID No. 3).

Suitable CDR2 of the variable heavy domain (VH) of the monoclonal antibody is TYYRSKWYN (SEQ ID No. 4).

Suitable CDR3 of the variable heavy domain (VH) of the monoclonal antibody is ARQGSTYFDY (SEQ ID No. 5).

Suitable CDR1 of the variable light domain (VL) of the monoclonal antibody is QTISSS (SEQ ID No. 6).

Suitable CDR2 of the variable light domain (VL) of the monoclonal antibody is SAS (SEQ ID No. 7).

Suitable CDR3 of the variable light domain (VL) of the monoclonal antibody is QQTYSAPPT (SEQ ID No. 8).

In one embodiment, the monoclonal antibody of the present invention is humanized. The monoclonal antibody of the present invention can be humanized by modifying the amino acid sequence of the antibody. Methods to reduce the immunogenicity of the specific binding molecules of the invention include CDR grafting on to a suitable antibody framework scaffold or variable surface residues remodeling, e.g. by site directed mutagenesis or other commonly used molecular biological techniques. A humanized antibody may be a modified antibody having the variable regions of a non-human, e.g. murine, antibody and the constant region of a human antibody. In one embodiment, the monoclonal antibody of the present invention is a human monoclonal antibody.

In another advantageous embodiment, the specific binding molecule of the invention can be a fragment of an antibody. It has been shown that fragments of a whole antibody can perform the function of binding antigens. Examples of binding fragments are:
(i) the Fab fragment consisting of VL, VH, CL and CH1 domains;
(ii) the Fd fragment consisting of the VH and CH1 domains;
(iii) the Fv fragment consisting of the VL and VH domains of a single antibody;
(iv) the dAb fragment, which consists of a $V_H$ domain;
(v) isolated CDR regions;
(vi) F(ab')2 fragments, a bivalent fragment comprising two linked Fab fragments
(vii) single chain variable fragment molecules (scFv), wherein a VH domain and a VL domain are linked by a peptide linker which allows the two domains to associate to form an antigen binding site;
(viii) bispecific single chain Fv dimers and
(ix) "diabodies", multivalent or multispecific fragments constructed by gene fusion.
(x) scFv-Fc consisting in two scFv fragments with a Fc portion As used herein, the term "CH1 domain" includes the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule, and does not form a part of the Fc region of an immunoglobulin heavy chain.

As used herein, the term "CL domain" comprises the constant region domain of an immunoglobulin light chain that extends, e.g. from about Kabat position 107A-216 (EU positions 108-214 (kappa)). The Eu/Kabat conversion table for the Kappa C domain is provided below. The CL domain is adjacent to the VL domain and includes the carboxy terminal of an immunoglobulin light chain.

In a preferred embodiment, the specific binding molecule of the invention is a single chain variable fragment (scFv) molecule. Within the context of the invention, the term "single chain variable fragment" or "scFv molecule" or "scFv fragment" or "scFv antibody" or "scFv" refers to a single folded polypeptide comprising the VH and VL domains of an antibody linked through a peptide linker. In such a scFv molecule, the VH and VL domains can be either in the VH-linker-VL or VL-linker-VH order. In addition to facilitate its production, a scFv molecule may contain a tag molecule linked to the scFv via a spacer. A scFv molecule thus comprises the VH and VL domains implicated into antigen recognizing but not the immunogenic constant domains of corresponding antibody.

By a "peptide linker" is meant a flexible peptide that permits an appropriate folding of the scFv molecule, i.e. an appropriate folding of the VH and VL domains and their capacity to be brought together. In addition, such a peptide linker should permit folding into a monomeric functional unit. Advantageously, the peptide linker is located between the variable heavy domain (VH) and the variable light domain (VL). When the scFv is assembled in the VH to VL orientation (VH-linker-VL), a scFv with a linker of 3 to 12 residues cannot fold into a functional Fv domain and instead associates with a second molecule to form a bivalent dimer. Reducing below 3 residues leads to trimers. In this case, a suitable linker should thus have at least 12 and preferably less than 25 amino acids, preferably between 15 and 25 amino acids, preferably between 16 and 22 amino acids, or preferably between 18 and 21 amino acids, and should preferably comprise a high percentage of glycine residues with respect to the amino acid sequence of the suitable linker, preferably at least 50% of the amino acids of the suitable linker are glycine residues. An 18 amino acid residues linker is the minimal sequence size that can be used. A suitable peptide linker should then have between 18 and 25 amino acids, preferably between 18 and 21 amino acids. Advantageously, the suitable peptide linker of the invention has 18 amino acids. Examples of suitable peptide linkers include peptides having at least 85% identity to SEQ ID No. 9. Advantageously, peptide linkers include peptides having at least 90%, at least 91%, at least 92%, at least 93%, at least 94%, at least 95%, at least 96%, at least 97%, at least 98%, at least 98.5%, at least 99% identity to SEQ ID No. 9. An example of a suitable linker is linker of sequence EFGGGGSGGGGSGGGGSR (SEQ ID No. 9).

In a particular advantageous embodiment, the single-chain variable fragment (scFv) molecule which specifically binds to galectin-3 protein, comprises:
- a variable heavy domain (VH) comprising an amino acid sequence having at least 90% identity to SEQ ID No. 1,
- a peptide linker comprising an amino acid sequence having at least 85% identity to SEQ ID No. 9, and
- a variable light domain (VL) comprising an amino acid sequence having at least 90% identity to SEQ ID No. 2.

In an advantageous embodiment, the variable heavy domain (VH) of the single-chain variable fragment (scFv) molecule comprises an amino acid sequence having at least 90% identity to SEQ ID No. 1. Advantageously, the variable heavy domain (VH) of the single-chain variable fragment (scFv) molecule comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 1. In a particular advantageous embodiment, the variable heavy domain (VH) of the single-chain variable fragment (scFv) molecule has the amino acid sequence SEQ ID No. 1. Suitable variable heavy domain (VH) of the scFv molecule is (SEQ ID No. 1)
QVQLQQSGPGLVKPSQTLSLTCAISGDSVSSNNFGWNWIRQSPSRGLEWL

GRTYYRSKWYNDYAVSVRSRITINPDTSKNQFSLQLNSVTPEDTAVYYCA

RQGSTYFDYWGQGTLVTVSS.

In an advantageous embodiment, the variable light domain (VL) of the single-chain variable fragment (scFv) molecule comprises an amino acid sequence having at least 90% identity to SEQ ID No. 2. Advantageously, the variable light domain (VL) of the single-chain variable fragment (scFv) molecule comprises an amino acid sequence having at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 2. In a particular advantageous embodiment, the variable light domain (VL) of the single-chain variable fragment (scFv) molecule has the amino acid sequence SEQ ID No. 2. Suitable variable light domain (VL) of the scFv molecule is (SEQ ID No. 2)
DIVMTQSPSSLSASVGDRVTITCRASQTISSSLAWFQQRPGEAPNLLIYS

ASSLQSGVPSRFSGSGSGTDFTLTISSLQPEDFATYSCQQTYSAPPTFGG

GTKLEIK.

In an advantageously embodiment, the single-chain variable fragment (scFv) molecule which specifically binds to galectin-3 protein, comprises:
 a variable heavy domain (VH) having the amino acid sequence SEQ ID No. 1,
 a peptide linker having the amino acid sequence SEQ ID No. 9, and
 a variable light domain (VL) having the amino acid sequence SEQ ID No. 2.

Advantageously, the scFv molecule directed to galectin-3 protein comprises:
 a variable heavy domain (VH) of SEQ ID No. 1, comprising CDR1, CDR2 and CDR3 regions constituted of SEQ ID No. 3, SEQ ID No. 4 and SEQ ID No. 5,
 a peptide linker having the amino acid sequence SEQ ID No. 9, and
 a variable light domain (VL) of SEQ ID No. 2, comprising CDR1, CDR2 and CDR3 regions constituted of SEQ ID No. 6, SEQ ID No. 7 and SEQ ID No. 8.

Suitable CDR1 of the variable heavy domain (VH) of the scFv molecule is GDSVSSNNFG (SEQ ID No. 3).

Suitable CDR2 of the variable heavy domain (VH) of the scFv molecule is TYYRSKWYN (SEQ ID No. 4).

Suitable CDR3 of the variable heavy domain (VH) of the scFv molecule is ARQGSTYFDY (SEQ ID No. 5).

Suitable CDR1 of the variable light domain (VL) of the scFv molecule is QTISSS (SEQ ID No. 6).

Suitable CDR2 of the variable light domain (VL) of the scFv molecule is SAS (SEQ ID No. 7).

Suitable CDR3 of the variable light domain (VL) of the scFv molecule is QQTYSAPPT (SEQ ID No. 8).

In a preferred embodiment, said scFv molecule according to the invention can further comprises a peptide tag, useful for purification or for functionalize surface, notably in case of grafting of the scFv molecule to a nano-object, and optionally a short peptide spacer between the core scFv antibody (comprising the VH and VL domains and the peptide linker) and the peptide tag.

Examples of suitable peptide tags for purification include His6Tag (HHHHHH, SEQ ID No. 15), a protein C tag (HPC4) (EDQVDPRLIDGK, SEQ ID No. 16), strep tag (WSHPQFEK, SEQ ID No. 17), V5 epitope tag (GKPIPN-PLLGLDST, SEQ ID No. 18), a short version of V5 epitope tag (IPNPLLGLD, SEQ ID No. 19) or c-myc tag (EQKLI-SEEDL, SEQ ID No. 20). Examples of suitable peptide tags for functionalize surface, notably in case of grafting of the scFv molecule to a nano-object include sortase LPETG (GGGGSLPETGGAA, SEQ ID No. 21), IgM-Tail (PT-LYNVSLVMSDTAGTCY, SEQ ID No. 23) or CC-Tag (GGGGSCCAA, SEQ ID No. 22).

Examples of suitable peptide spacers include peptides having at least 85% identity to SEQ ID No. 24. Advantageously, peptide spacers include peptides having at least 90%, at least 91%, at least 92%, at least 93%, at least 94%, at least 95%, at least 96%, at least 97%, at least 98%, at least 98.5%, at least 99% identity to SEQ ID No. 24.

An example of a suitable peptide spacer is peptide spacer of sequence (SEQ ID No. 24)
GGTGGCGGTGGCTCGGGCGGTGGTGGGTCTGGTGGCGGCGGT.

In a preferred embodiment, said scFv molecule according to the invention is a fully human scFv molecule.

In a preferred embodiment, the invention concerns a specific binding molecule directed against galectin-3 protein, comprising or consisting of an amino acid sequence having at least 85%, at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity with SEQ ID No. 10, in which amino acids 1 to 120 and 139 to 245 of said 245 amino acids sequence are constituted of SEQ ID No. 1 and SEQ ID No. 2 respectively.

In a particular embodiment, the invention concerns an antibody directed against galectin-3 protein, comprising or consisting of an amino acid sequence having at least 85%, at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity with SEQ ID No. 10, in which amino acids 1 to 120 and 139 to 245 of said 245 amino acids sequence are constituted of SEQ ID No. 1, and SEQ ID No. 2 respectively.

In a particular embodiment, the invention concerns a scFv molecule directed against galectin-3 protein, comprising or consisting of an amino acid sequence having at least 85%, at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity with SEQ ID No. 10, in which amino acids 1 to 120, 121 to 138, and 139 to 245 of said 245 amino acids sequence are constituted of SEQ ID No. 1, SEQ ID No. 9, SEQ ID No. 2 respectively.

The present invention also relates to a nucleic acid sequence encoding a specific binding molecule as described above.

In a particular embodiment, the nucleic acid sequence encoding the specific binding molecule comprises at least 85% identity to the nucleic acid sequence SEQ ID No. 11. Advantageously, the nucleic acid sequence comprises at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to the nucleic acid sequence SEQ ID No. 11. In a particular embodiment, the nucleic acid sequence encoding the specific binding molecule has the nucleic acid sequence SEQ ID No. 11.

In a particular embodiment, said specific binding molecule comprises or consists of SEQ ID No. 10, and the nucleic acid sequence of the specific binding molecule comprises or consist of SEQ ID No. 11, or any derived nucleic sequence encoding SEQ ID No. 10, for instance as a result of the degeneracy of the genetic code.

Another object of the invention is an expression vector, for example a viral or plasmid vector, comprising a nucleic acid sequence encoding the specific binding molecule such as defined herein. In the context of the invention, the term "vector" refers to a polynucleotide sequence containing a desired coding sequence and control sequences in operable linkage, so that hosts transformed with these sequences are capable of producing the encoded proteins. The vector may replicate autonomously in the chosen host cell, or it may be an integrative vector for the host cell in question. Such vectors are prepared by methods familiar to one of skill in the art, and the resulting clones may be introduced into a suitable host cell by standard methods, such as lipofection, electroporation, nucleofection, use of gene gun, polycationic agents, heat shock, or chemical methods.

Another object of the invention is a host cell transfected with said vector or vectors. The host cell may be selected from among prokaryotic or eukaryotic systems, for example bacterial cells but also yeast cells or animal cells, in particular mammalian cells. Insect cells or plant cells may also be used.

In a particular embodiment of the invention, when the specific binding molecule is an antibody, the antibody may thus be produced by recombination in a host cell, transformed with one or more vectors which allow the expression and/or the secretion of the nucleotide sequences coding for the heavy chain and/or the light chain of the antibody. The vector usually comprises a promoter, translation initiation and termination signals, as well as suitable transcription regulation regions. It is maintained in a stable manner in the host cell and may optionally have specific signals that specify the secretion of the translated protein. These various elements are selected and optimized by the person skilled in the art according to the host cell used. Such vectors are prepared by methods commonly used by the person skilled in the art, and the resulting clones may be introduced into a suitable host by standard methods, such as lipofection, electroporation, nucleofection, the use of gene gun, of polycationic agents, heat shock or chemical methods. The host cell may be selected from prokaryotic or eukaryotic systems, for example bacterial cells but also yeast cells or animal cells, in particular mammalian cells. The preferred mammalian cells for the production of the monoclonal antibody are the rat line YB2/0, the hamster line CHO, in particular the lines CHO dhfr- and CHO Lec13, PER.C6™, EB66, HEK293, K562, NS0, SP2/0, BHK or COS. It is also possible to use insect cells such as S2, Sf9, Sf21. Another mode of production is the expression of the recombinant antibody in transgenic organisms, for example in plants or particularly in the milk of transgenic animals such as rabbit, goat or pig. Transgenic milk can also be used as a method for the production of recombinant antibodies.

According to a preferred embodiment, the antibody is produced in the milk of non-human transgenic mammals, genetically modified to produce this glycoprotein. The mammal may be for example a goat, a ewe, a female bison, buffalo, camel, llama, mouse or rat, or a cow, sow, doe rabbit or mare.

Secretion of the antibody by the mammary glands, allowing its presence in the milk of the transgenic mammal, involves tissue-dependent control of the expression of the antibody. Such methods of control are well-known to the person skilled in the art. Expression is controlled by means of sequences allowing expression of the glycoprotein in a particular tissue of the animal. They are in particular promotor sequences of the "WAP", "beta-casein", "beta-lacto-globulin" type and possibly sequences of the peptide signal type. Preferably, the antibody is produced in the mammary glands of a transgenic goat, using an expression vector comprising the sequence of the coding sequences needed for the production of the protein which are under the control of a 5' beta-casein promoter. A process for extracting proteins of interest from the milk of transgenic animals is described in the patent EP 0 264 166.

Advantageously, more than 4 grams of antibody per liter of milk is produced, advantageously more than 5, 10, 15, 20, 25, 30, 35 grams per liter, advantageously up to 70 grams per liter.

In a particular embodiment of the invention, when the specific binding molecule is a scFv molecule, the scFv molecule can be produced by implementing the following steps:
1) a step of preparing a scFv molecule library composed of phage clones, each one of which expresses a scFv molecule on the surface;
2) a step of selecting a phage clone expressing a scFv molecule capable of binding to the relevant antigen ("scFv-phage") by screening the scFv molecule library with an antigen.

In an advantageously embodiment, the scFv molecule library of step 1) is obtained according to the method disclosed in WO 2007/137616. Briefly, the method disclosed in WO 2007/137616 comprises a step of performing random mutagenesis of a polynucleotide encoding the variable region of a heavy chain and/or the variable region of a light chain, wherein random mutagenesis is performed on a library of polynucleotides comprising a sequence encoding the variable region of a heavy chain and/or the variable region of a light chain; and wherein the random mutagenesis process creates randomly distributed mutations along at least 70% of the sequence encoding the variable region.

According to a particularly advantageously embodiment, the scFv molecule library is expressed by phage display and selected in vivo and the relevant antigen is galectin-3 protein.

According to a particularly advantageously embodiment, the scFv-phages were obtained from the scFv-phagemid combinatorial library by expression of the scFv on the phage surface, following the addition of a helper filamentous phage to recombinant phagemid infected bacteria in the exponential phase. Three rounds of biopanning were performed in atheromatous injured rabbits. Briefly, the procedure was the following: $2.4 \times 10^{12}$ colony-forming units (cfu) of scFv-phages were injected into an atheromatous rabbit. After 1 h in circulation, the animal was sacrificed, the aorta was retrieved and scFv-phages binding to the aorta were eluted in different fractions. The eluted scFv-phages were re-amplified in XL1-Blue bacteria and following scFv expression at the phage surface as above, the amplified scFv-phages were re-injected in another atheromatous animal. Rounds 2 and 3 were conducted following the same procedure. The number of re-injected colony-forming units were $4.8 \times 10^{11}$ in round 2 and $3.9 \times 10^{11}$ in round 3.

Then, the scFv-phages are amplified in XL1-Blue bacteria, in particular XL1-blue *E. coli*, and the cells are pelleted and plated on ampicillin, in particular at a concentration comprises between 50 µg/ml and 200 µg/ml, advantageously at 100 µg/ml and glucose, in particular at a concentration comprises between 1% (w/v) and 4% (w/v), advantageously at 2% (w/v), containing 2×TY agar (2TYGA) and incubated at least 10 hours, advantageously 16 hours, at a temperature comprises between 20° C. and 40° C., advantageously at 30° C. After the third round of biopanning, plated clones are individually picked into deep well masterblocks filled with 2TYGA selective medium for FACS screening.

Another object of the invention concerns a fusion protein comprising the specific binding molecule as described above and a human immunoglobulin G (IgG) Fc fragment. Advantageously, the human immunoglobulin G (IgG) Fc fragment is a human IgG1 Fc fragment. In a particular embodiment, the human immunoglobulin G (IgG) Fc fragment comprises an amino acid sequence having at least 85% identity to SEQ ID No. 12. Advantageously, the human immunoglobulin G (IgG) Fc fragment comprises an amino acid sequence having at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 12. In a particular advantageous embodiment, the human immunoglobulin G (IgG) Fc fragment has the amino acid sequence SEQ ID No. 12.

In one embodiment, the fusion protein comprises an amino acid sequence having at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 13. In a particular embodiment, the amino acid sequence of the fusion protein is SEQ ID No. 13.

In one embodiment, the fusion protein comprises a nucleic acid sequence having at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8%, at least 99.9% identity to SEQ ID No. 14.

In preferred embodiment, the nucleic acid sequence encoding the fusion protein has the nucleic acid sequence SEQ ID No. 14.

In preferred embodiment, said fusion protein comprises or consists of SEQ ID No. 13, and said nucleic acid sequence comprises or consist of SEQ ID No. 14, or any derived nucleic sequence encoding SEQ ID No. 13, for instance as a result of the degeneracy of the genetic code.

The construction of fusion proteins in the invention is based on conventional molecular cloning technology. PCR synthesis method was used to clone a DNA encoding the above fusion protein into a vector. The vector for expressing the fusion protein may be a plasmid commonly used in molecular biology. A signal peptide sequence is included at the front of the amino terminus of the fusion protein so as to insure protein secretion from cells. The vector sequence includes a promoter for driving gene expression, start and stop signals for protein translation, as well as polyadenylation (polyA) sequence. The vector may include an antibiotics resistance gene to facilitate plasmid replication in bacteria. In addition, the vector may also include an eukaryotic cell selection gene for the selection of stable transfected cell strains.

After the construction of plasmid, DNA sequence of the fusion protein is confirmed by sequencing. Then corresponding protein can be expressed by the transfection of the plasmid DNA into cells. Many expression systems are available for expressing such fusion proteins, which include but are not limited to mammalian cells, bacteria, yeast, insect cells, etc.

In a preferred embodiment of the invention, the fusion protein comprises an scFv molecule and a human immunoglobulin G (IgG) Fc fragment, as respectively described above.

The present invention also relates to a specific binding molecule or the fusion protein as defined above, for its use as a medicament. In particular, the present invention relates to specific binding molecule or the fusion protein, for its use in the diagnosis, prophylaxis and/or the treatment of inflammatory disease, atherosclerosis, chronic kidney diseases (Rebholz et al., Kidney international, 31 Aug. 2017, "Plasma galectin-3 level are associated with the risk of incident chronic kidney disease"), atrial fibrillation (Takemoto et al., JACC Basic Transl Sci., 2016, vol 1 (3), pages 143-154: "Galectin-3 regulates atrial fibrillation remodeling and predicts catheter ablation outcomes"), cancer (Fang et al. 2017), notably thyroid tumor (D'alessandria et al. 2016) or colorectal cancer (Tao et al. 2017), hypertrophic cardiomyopathy (Gawor et al. 2017), HIV infection (Xue et al. 2017; Wang et al. 2014).

The term "prevention" or "prophylaxis" or "preventative treatment" or "prophylactic treatment" comprises a treatment leading to the prevention of a disease as well as a treatment reducing and/or delaying the incidence of a disease or the risk of it occurring.

According to the invention, the specific binding molecule or the fusion protein is particularly useful for preventing or reducing the formation or the progression of atheroma plaques despite high serum cholesterol.

The term "treatment" or "curative treatment" is defined as a treatment leading to a cure or a treatment which alleviates, improves and/or eliminates, reduces and/or stabilizes the symptoms of a disease or the suffering that it causes.

According to the invention, the specific binding molecule or the fusion protein is particularly useful for treating atherosclerosis, chronic kidney diseases, atrial fibrillation, cancer, notably thyroid tumor or colorectal cancer, hypertrophic cardiomyopathy, HIV infection, by inhibiting or antagonizing galectin-3 protein and thus leading to the reduction of the formation or the progression of atheroma plaques, in particular to the reduction of the atheroma plaque volume despite high serum cholesterol.

Another object of the invention concerns a pharmaceutical composition comprising a pharmaceutically effective amount of the specific binding molecule or the fusion protein as defined above as an active substance and at least one pharmaceutically acceptable carrier.

Advantageously, the pharmaceutical composition comprising a therapeutically effective amount of the specific binding molecule or the fusion protein as defined above as an active substance is administered to a subject suffering from or suspected of suffering from inflammatory disease. More preferably, the inflammatory disease is atherosclerosis.

In one embodiment the subject is a human. In another embodiment the subject is a non-human animal, e.g., a dog, cat, horse, cow, pig, sheep, goat or primate.

According to embodiments that involve administering to a subject in need of treatment a therapeutically effective amount of the antibodies as provided herein, "therapeutically effective" or "an amount effective to treat" or "pharmaceutically effective" denotes the amount of specific binding molecule or fusion protein or of a composition needed to inhibit or reverse a disease condition (e.g., to treat inflammatory disease and preferably atherosclerosis). Determining a therapeutically effective amount specifically depends on such factors as toxicity and efficacy of the medicament. These factors will differ depending on other factors such as potency, relative bioavailability, patient body weight, severity of adverse side-effects and preferred mode of administration. Toxicity may be determined using methods well known in the art. Efficacy may be determined utilizing the same guidance. Efficacy, for example, can be measured by a decrease of atheroma plaque volume. A pharmaceutically effective amount, therefore, is an amount that is deemed by the clinician to be toxicologically tolerable, yet efficacious.

Dosage may be adjusted appropriately to achieve desired drug (e.g., specific binding molecule or fusion protein) levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day may also be employed to achieve appropriate systemic levels of antibodies. Appropriate systemic levels can be determined by, for example, measurement of the patient's peak or sustained plasma level of the drug. "Dose" and "dosage" are used interchangeably herein.

In some embodiments, the amount of specific binding molecule or the fusion protein or pharmaceutical composition administered to a subject is 0.1 mg to 500 mg/kg, every week or every 2 week or every 4 week or every 8 weeks, 1 to 400 mg/kg every week or every 2 week or every 4 week or every 8 weeks, or 5 to 300 mg/kg every week or every 2 week or every 4 week or every 8 weeks.

In other embodiments, the amount of specific binding molecule or the fusion protein or pharmaceutical composition administered to a subject is in doses varying from approximately 0.05 mg/m$^2$ to 2,000 mg/m$^2$ in particular from 10 mg/m$^2$ to 2,000 mg/m$^2$, in particular, the unit dose administered can varying from 15 mg to approximately 3 g per patient.

The unit dose administered can vary from 100 µg to approximately 1 g per patient.

In some embodiments, the compositions provided are employed for in vivo applications. Depending on the intended mode of administration in vivo the compositions used may be in the dosage form of solid, semi-solid or liquid such as, e.g., tablets, pills, powders, capsules, gels, ointments, liquids, suspensions, or the like. Preferably, the compositions are administered in unit dosage forms suitable for single administration of precise dosage amounts. The compositions may also include, depending on the formulation desired, at least one pharmaceutically acceptable carrier or diluent, which are defined as aqueous-based vehicles commonly used to formulate pharmaceutical compositions for animal or human administration. The diluent is selected so as not to affect the biological activity of the specific binding molecule or the fusion protein of interest. Examples of such diluents are distilled water, physiological saline, Ringer's solution, dextrose solution, and Hank's solution. The same diluents may be used to reconstitute a lyophilized recombinant protein of interest. In addition, the pharmaceutical composition may also include other medicinal agents, pharmaceutical agents, carriers, adjuvants, nontoxic, non-therapeutic, non-immunogenic stabilizers, etc. Effective amounts of such diluent or carrier are amounts which are effective to obtain a pharmaceutically acceptable formulation in terms of solubility of components, biological activity, etc. In some embodiments the compositions provided herein are sterile.

Administration during in vivo treatment may be by any routes, including oral, parenteral, intramuscular, intranasal, sublingual, intratracheal, inhalation, ocular, vaginal, and rectal. Intracapsular, intravenous, and intraperitoneal routes of administration may also be employed. The skilled artisan recognizes that the route of administration varies depending on the disorder to be treated. For example, the compositions or specific binding molecule or fusion proteins herein may be administered to a subject via oral, parenteral or topical administration. In one embodiment, the compositions or specific binding molecule or fusion proteins herein are administered by intravenous infusion.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compositions in water soluble form. Additionally, suspensions of the active compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions. Alternatively, the active compositions may be in powder form for constitution with a suitable vehicle, e.g., sterile pyrogen-free water, before use.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. The component or components may be chemically modified so that oral delivery of the antibodies is efficacious. Generally, the chemical modification contemplated is the attachment of at least one molecule to the antibodies, where said molecule permits (a) inhibition of proteolysis; and (b) uptake into the blood stream from the stomach or intestine. Also desired is the increase in overall stability of the antibodies and increase in circulation time in the body. Examples of such molecules include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. Preferred for pharmaceutical usage, as indicated above, are polyethylene glycol molecules. For oral compositions, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the antibody or by release of the biologically active material beyond the stomach environment, such as in the intestine.

For buccal administration, the compositions may take the form of tablets or lozenges formulated in conventional manner.

For administration by inhalation, the compositions for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compositions and a suitable powder base such as lactose or starch.

Also contemplated herein is pulmonary delivery. The compositions can be delivered to the lungs of a mammal while inhaling and traverses across the lung epithelial lining to the blood stream. Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Nasal delivery of a pharmaceutical composition disclosed herein is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

The compositions may also be formulated in rectal or vaginal compositions such as suppositories or retention enemas, e.g., containing conventional suppository bases such as cocoa butter or other glycerides.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

Another subject of the invention relates to a method for the preventative treatment of inflammatory disease in patients in need of, comprising the administration to said patients of a specific binding molecule or a fusion protein or a pharmaceutical composition comprising a therapeutically effective amount of a specific binding molecule or a fusion protein as an active substance and at least one pharmaceutically acceptable carrier as defined above. More preferably, the inflammatory disease is atherosclerosis.

In a particular advantageous embodiment, the present invention relates to the use of a pharmaceutical composition comprising a therapeutically effective amount of a specific binding molecule or a fusion protein as an active in the manufacture of a medicinal product intended for the prevention of inflammatory disease.

In a particular advantageous embodiment, the present invention relates to the use of a pharmaceutical composition comprising a therapeutically effective amount of a specific binding molecule or a fusion protein as an active in the manufacture of a medicinal product intended for the prevention of atherosclerosis.

Another subject of the invention relates to a method for treating inflammatory disease in patients in need of, comprising the administration to said patients of a specific binding molecule or a fusion protein or a pharmaceutical composition comprising a therapeutically effective amount of a specific binding molecule or a fusion protein as an active substance and at least one pharmaceutically acceptable carrier as defined above. More preferably, the inflammatory disease is atherosclerosis.

In a particular advantageous embodiment, the present invention relates to the use of a pharmaceutical composition comprising a therapeutically effective amount of a specific binding molecule or a fusion protein as an active in the manufacture of a medicinal product intended for the treatment of inflammatory disease.

In a particular advantageous embodiment, the present invention relates to the use of a pharmaceutical composition comprising a therapeutically effective amount of a specific binding molecule or a fusion protein as an active in the manufacture of a medicinal product intended for the treatment of atherosclerosis.

The present invention also relates to a specific binding molecule or a fusion protein as defined above, for use as a diagnostic agent. Advantageously, the specific binding molecule or the fusion protein as defined above for the preparation of a diagnostic composition for medical imaging, or for diagnostic monitoring of the efficacy of a therapeutic treatment, and to a diagnostic method comprising the administration of a pharmaceutically acceptable amount of the specific binding molecule or the fusion protein as mentioned above. Example of medical imaging systems include, but are not limited to, computed tomography (CT) systems, X-ray systems (including both conventional and digital or digitized imaging systems, including computed radiography (CR)), magnetic resonance (MR) systems, positron emission tomography (PET) systems, ultrasound systems, and nuclear medicine systems.

For diagnosis in Magnetic Resonance Imaging (MRI), the intravenous administration by injection usually as a saline solution is typically performed at a dose of from 1 to 500 µmol Gd/kg (examples: gadolinium based molecules: Magnevist®—100-300 µmol Gd/kg—, Dotarem®—100 µmol Gd/kg—; Iron oxide based molecules: Endorem® (15 µmol Fe/kg), Sinerem® (45 µmol Fe/kg); Resovist® (13 µmol Fe/kg); Ferumoxsil® or Lumirem® (6 µmol Fe/kg); Feridex® (15 µmol Fe/kg)). The pharmaceutically acceptable unit doses will depend on the nature of the chelate, the route of administration, and on the patient and especially on the nature of the disorder to be studied. For an intravenous injection and observation by magnetic resonance, the concentration of the specific binding molecule or the fusion will typically be between 0.001 and 0.5 mol/litre, and from 0.001 to 0.1 mmol/kg will be administered to the patient, depending on the case. Higher clinical doses may also be practiced, for example a triple dose (0.3 mmol/kg). The administration rate, the concentration, the speed of injection are adapted according to the clinical indication and product specifications, and eventually also in view of the behaviour of the contrast agent during the MRI procedure. Any appropriate protocol is used, with possible adjustment of the administration in view of the patient data, of first test injections operated, of the enhancement curves obtained. The speed of injection may be calculated (advantageously automatically by data treatment tools) according to the protocol and during the protocol in view of the relaxivity curve during the course of the acquisition; for instance if the administration rate/speed is not sufficient for optimal enhancement considering the data base, the injector automatically increases this rate during the MRI procedure.

In an advantageously embodiment, the present invention relates to a specific binding molecule or a fusion protein, for use in a method of diagnosis in vivo of inflammatory disease. In a particular advantageously embodiment, the present invention relates to a specific binding molecule y or a fusion protein, for use in a method of diagnosis in vivo of inflammatory disease, by using resonance magnetic imaging (RMI). More preferably, the inflammatory disease is atherosclerosis.

According to the invention, the specific binding molecule or the fusion protein is particularly useful for the diagnosis of atherosclerosis, by specifically binding galectin-3 protein, which is overexpressed in atherosclerotic inflammatory process in atherosclerosis, and thus leading to the identification of the formation or of the progression of atheroma plaques.

Another subject of the invention relates to a diagnostic composition comprising the specific binding molecule or the fusion protein as defined above as a diagnostic agent and a chemical nanoparticle as a "carrier". By "carrier", it is intended a chemical vehicle coupled to the binding protein or fusion protein to transport the chemical nanoparticle to the desired anatomical site. According to the present invention, the carrier can be in solid or liquid form. Examples of carrier include, but are not limited to, nanoparticles, such as metallic nanoparticles for example iron oxide, gold-iron oxide, iron-cobalt, iron-platinum nanoparticles, ferrites or complexes of lanthanide metals mostly containing gadolinium ions, magnetoliposomes, borocaptate sodium, magneto SLN (solid lipid nanoparticles), LON (lipid oil nanoparticles), magneto nanoemulsions oil in water, USPIO (ultra small paramagnetic iron oxide), near IR fluorochroms or radioactive molecules for PET imaging (F18, Cu64).

In a particular advantageously embodiment, the carrier is a nanoparticle. In a particular advantageously embodiment, the specific binding molecule or the fusion protein as defined above are grafted on the nanoparticles. In a particular advantageously embodiment, the diagnostic composition is used in a method of diagnosis in vivo of inflammatory disease, by using resonance magnetic imaging (RMI). More preferably, the inflammatory disease is atherosclerosis.

According to embodiments, these diagnostic compositions may be chosen to be administered in combination with or in place of prior-art diagnostic composition as a function of the diagnostic profile of the patient, and especially of the profile of tolerance of the patient to the contrast products. The choice may be made by the practician and/or automatically by any tagging system (RFID tag carried by the patient . . . ) and conditioning the type of administration, for example the choice of the contrast agent best adapted such as the formulation of the present application.

Another subject of the invention relates to a diagnostic kit for the detection of galectin-3 protein, preferably in patients suffering from or suspected of suffering from inflammatory disease, said kit comprising an injectable solution which comprises the specific binding molecule or the fusion protein as defined above. More preferably, the inflammatory disease is atherosclerosis.

According to the present invention, the diagnostic kit includes an injectable solution comprising the specific binding molecule or the fusion protein and carrier for selectively identifying atheroma lesions in the subject's body, and a delivery apparatus configured for administering intravenously an effective amount of the injectable solution to a subject to selectively identify a plurality of atheroma plaques in the subject's body.

According to the present invention, the diagnostic kit includes an injectable solution comprising the specific binding molecule or the fusion protein and fluorescent markers for selectively labeling atheroma lesions in the subject's body, and a delivery apparatus configured for administering intravenously an effective amount of the injectable solution to a subject to selectively label a plurality of atheroma plaques in the subject's body.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 2 shows the capacity of fusion protein produced in HEK cells to bind to paraffin-embedded atheromatous human, mouse and rabbit sections prepared from atheromatous specimens. Different areas of cross sections are identified: (a) Adventice, (M) Media, (I) Intima. P3 antibody were incubated with atherosclerotic rabbit, mouse and human tissue sections. The first line corresponds to the secondary antibody alone (anti human Fc HRP). The second line corresponds to the scFv-Fc P3. After addition of secondary goat anti-human Fc antibody, coupled to HRP, sections were revealed with DAB substrate kit reagent. The presence of the antigen recognized by the scFv-Fc P3 was indicated by dark staining. No staining was observed in the presence of secondary antibody. A low background staining only was noticed on human sections. Scale bars represent 100 μm. Nuclei were counterstained with hematoxylin.

FIG. 6 shows the capacity of specific binding molecule (IgG1) produced in HEK cells to bind to paraffin-embedded atheromatous human and mouse sections prepared from atheromatous specimens.

FIG. 7 shows the capacity of specific binding molecule (P3 scFv-Fc-2C antibody) grafted on nanoparticles containing iron-oxide to diagnose in vivo atherosclerosis, by using resonance magnetic imaging (RMI) on APOE–/– mice. a. Segmented R2* maps estimated at the plaque level, before (left) and after (right) the injection of SPIO-NE-P3 at 3 mgFe.Kg$^{-1}$ in ApoE$^{-/-}$ mice superimposed on their corresponding magnitude MR images (TE=4 ms). I. Black*: liver. b. Mean R2* values measured on 3 mice (Up to 8 slice per mouse; 23 slices in total). Error bar: standard error of the mean R2* measured on each slice (SEM).

DETAILED DESCRIPTION

Figure 1:
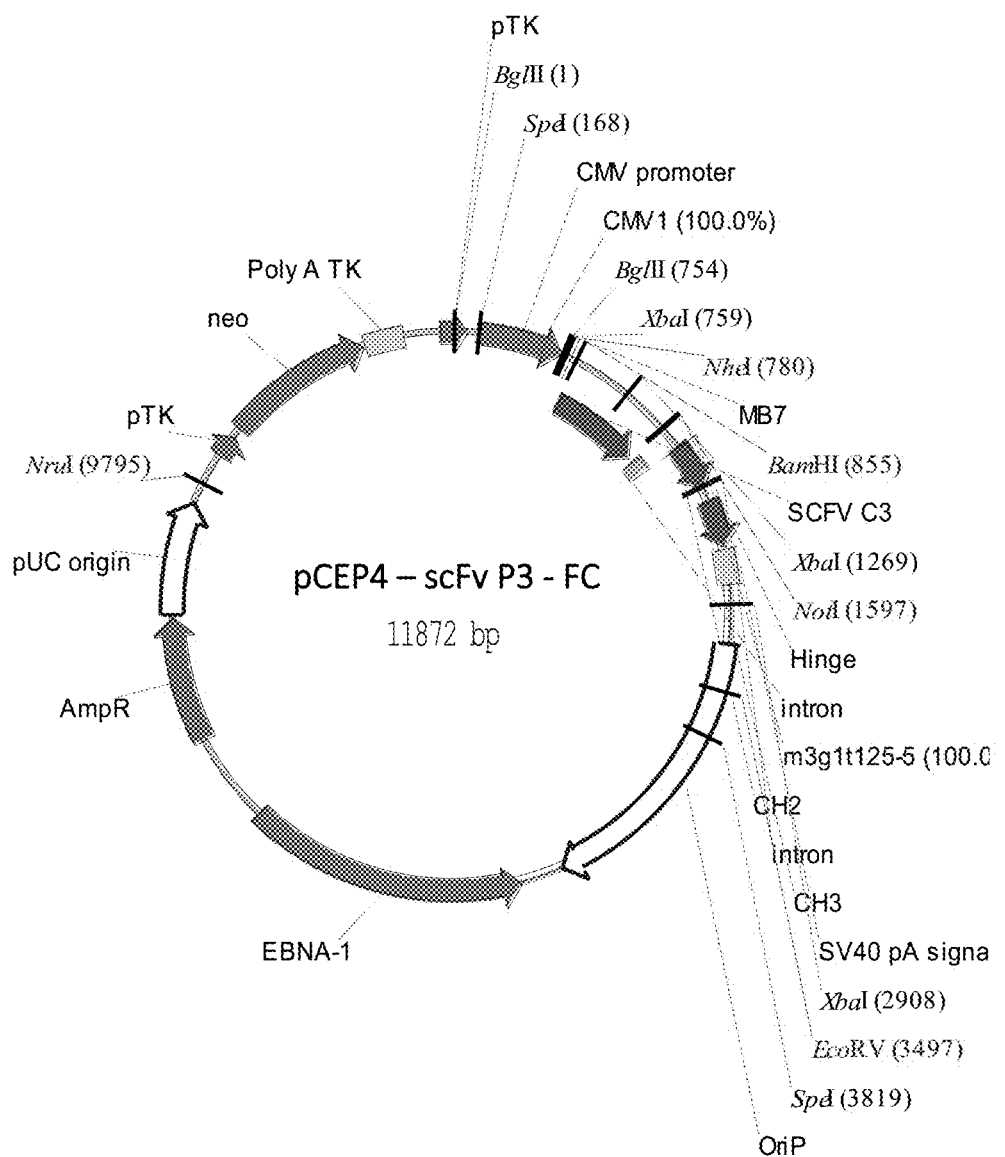
FIG. 1: Restriction card of vector of the specific binding molecule of the invention.

Example 1: In Vivo Phage Display Selection in the Atherosclerotic Rabbit Model

Complex Plaque Formation in the New Zealand Rabbit Animal Model

All animal experiments were performed in accordance with the Guide for the Care and Use of Laboratory Animals (NIH Publication No. 85-23, revised 1996) and were approved by the local ethics committee. The rabbit model was fed with a high cholesterol diet as previously described and two surgeries were performed, two months apart. The first consisted in a desendothelialization from the thoracic until the abdominal aorta and the second in an angioplasty carried out with a balloon through a femoral arteriotomy to the descendent thoracic aorta under radioscopic guidance.

In Vivo Phage Display Selection in the Atherosclerotic Rabbit Model

ScFv-Phage Library Preparation

The fully human recombinant fragment scFv antibody library described in patent WO2007137616 was used for in vivo phage display selection. For phage rescue, the phage library was infected with M13-KO7 helper phage (Invitrogen, France), followed by precipitation of phages with PEG/NaCl. After centrifugation at 11,000 g for 45 min at 4° C., the pellet containing scFv-phage particles was resuspended and filtered in a final volume of 500 μL sterile cold PBS.

In Vivo Phage-Display

Three rounds of biopanning were performed by phage display in atheromatous rabbits. The first selection was carried out using a continuous flow (150 μL/min) of 2.4× $10^{12}$ colony-forming units (cfu) of scFv-phages injected into the rabbit marginal ear vein for 30 min. After 1 h circulation, the animal was sacrificed and perfused via the heart with 120 mL of PBS to ensure phage clearance from the blood. The aorta was recovered from the aortic arch to the iliac bifurcations and divided into E1 (aortic arch and thoracic area) and E2 (abraded renal and abdominal areas) sections. Rounds 2 and 3 were conducted following the same procedure, excepted that the quantity of scFv-phages was lowered to 4.8×$10^{11}$ and 3.9×$10^{11}$ cfu respectively.

To access not only the scFv-phages binding to the endothelial cell surface but also those migrating into the intima and those internalized into cells invading the lesions, we respectively recovered F1, F2 and F3 fractions from aortic tissue.

The elution protocols of endothelial, intra-tissular and intra-cellular scFv fractions were performed according to Deramchia et al, with minor modifications. The endothelium cell surface-bound scFv-phage fraction (F1 fraction) was eluted with 500 μL of 0.1 M glycine-HCl, pH 2.2 and immediately neutralized with 15 μL of 2.5 M Tris-HCl, pH 8. The elution procedure was repeated and the different samples were pooled, a protease-inhibitor cocktail was added (ThermoScientific) and the faction was stored at 4° C. prior bacterial infection.

In order to elute intra-tissular scFv-phage fraction (F2 fraction), the aortic tissue was incubated with 900 μL of PBS (Ca2+, Mg2+ free) containing 2,000 U/mL of collagenase type II (Gibco) adjusted to 1 mL with 2.5% Trypsin-EDTA (Eurobio) and scratched using a glass slide to facilitate the tissue dissociation. Cycles of 20 s Polytron homogenizer (Ultraturax TP-20, Kinematica) were then performed at 4° C. to obtain a homogeneous solution. The homogenate was then incubated at 37° C. for 30 min with punctual vortexing and finally centrifuged for 10 minutes at 1,000 g to remove insoluble material. This preparation was homogenized 2 times more following the same procedure. After each centrifugation, supernatants containing eluted scFv-phages were collected and pooled in a clean tube in presence of a protease-inhibitor cocktail.

To access the internalized scFv-phage fraction (F3 fraction), the insoluble material was incubated with 500 μL of 0.1 M TEA (Tetraethylammonium chloride) (Sigma-Aldrich), pH 11.5 for 5 min at RT and then vigorously vortexed for another 5 min. Samples were neutralized by addition of 150 μL of 1M Tris-HCl, pH 7.4. After centrifugation at 1,000 g for 10 min, the supernatant was collected.

ScFv-phage fractions F1, F2 and F3 were separately rescued by infecting XL1-blue E. coli (Stratagene, France) (OD=0.5) and the cells were pelleted and plated on ampicillin (100 μg/mL) and glucose (2% (w/v)) containing 2×TY agar (2TYGA) and incubated 16 h at 30° C. Spreading on 145 mm Petri dishes has allowed constituting the glycerol stock and limiting dilutions on 80 mm dishes has allowed evaluating the enrichment of selection. After the third round of biopanning, plated clones were individually picked into deep well 96 masterblocks filled with 2TYGA selective medium (Greiner Bio one, France) for FACS screening and further analyses.

Phage Antibody Preparation

Individual phage-infected XL1 blue were grown in 96 deep well plates (Greiner Bio one, France) in 500 µL 2×TY/ampicillin/5% glucose supplemented with tetracycline at 10 µg/mL. After overnight incubation, 25 µL of bacterial culture were inoculated with 500 µL 2×TYGAT and incubated for 3 hrs. Phage production was induced by adding 25 µL of 2TY containing $3 \cdot 10^8$ helper phages (Stratagene, France). After infection for 1 h at 37° C., bacteria were pelleted and resuspended in 500 µL 2×2TYGA supplemented with kanamycin at 40 µg/mL for last growth at 26° C. under rotation (Newbrunswik, Edison, USA). Bacteria were then spun down at 10,000 g, 10 min, and supernatants used immediately for flow cytometry assay.

Example 2: Recombinant Antibody Engineering: HEK Cell or Insect Cell Expression, Purification and Characterization 1. Production and Purification from Insect Cells Fusion protein ScFv-Fc was produced using the baculovirus-insect cell system. Briefly, the cDNA encoding the scFv of the invention was amplified by PCR using the following primers: For P3/A-VH 5' GCTA CTTAAG GGT GTC CAG TGC CAGGTGCAGCTGCAGCAGTCTGGACCCGG 3' (SEQ ID No. 25); P3/A-VL 5' GCTA CGTACG CTTGAT-TTCCAGCTTGGTGCCGCCT 3' (SEQ ID No. 26) and ScFvP3-Fc as a template The PCR fragment was then inserted into a specific transfer vector in frame with a sequence encoding an IgG1 signal peptide at the 5' end and with a cDNA encoding a human IgG1 Fc domain with 2 extra cysteine residues at the C-terminal end.

Sf9 cells were cotransfected by lipofection with the transfer vector and purified viral DNA in the presence of 40 µl of DOTAP liposomal transfection reagent (Roche) (P. L. Feigner, G. M. Ringold. Cationic liposome-mediated transfection. Nature, 337, 1989, p. 387-388). Recombinant viruses were isolated by plaque assay and productive clones were screened by ELISA. The genomic organization of recombinant viruses was controlled by Southern blotting. Sequence of integrated genes was verified after amplification by PCR and sequencing (Eurofins Genomics, Germany).

ScFv-Fc was produced by infecting Sf9 cells adapted to grow in serum free medium, with the selected recombinant virus at a multiplicity of infection of 3 plaque forming units (PFU)/cell. Three days post-infection, cell culture supernatant was harvested and scFv-Fc was purified on HiTrap FF, protein A as recommended by the manufacturer (GE Healthcare) on AKTA Purifer. The quality of the purified scFv-Fc was assessed by SDS-PAGE and silver staining, ScFv preparation was sterilized after filtration on 0.22 µm membrane (Millex GP, Millipore) and stored at 4° C. prior usage.

2. Production and Purification from HEK Cells

ScFv-Fc was produced by transient transfection using the FreeStyle™ 293-F expression system (Invitrogen, France). Expression vector (FIG. 1) was prepared by first synthetizing (Invitrogen GeneArt) the cDNA fragment coding the scFv as linear fragment with optimized codons for *Homo sapiens*. The fragment was then subcloned by recombination using Infusion kit in between BamHI and NotI restriction sites of a pCEP4 vector (Invitrogen) containing signal peptide and a human IgG1 Fc fragment. HEK FreeStyle cells were transfected with the purified expression vector according to the supplier instruction with PEI 250 kDa (Sigma-Aldrich) in a 1/2 ratio (DNA/transfection reagent). After 7 days of production at 37° C. 8% $CO_2$, in F17 medium supplemented with 8 mM Glutamine, the supernatant was harvested, clarified by centrifugation and sterilely filtered at 0.2 µm prior to dosage by ELISA using FastELISA kit (RD Biotech, France) for human IgG. When scFv-Fc were used as purified molecules, this was performed by a one-step affinity chromatography with HiTrapp FF, protein A (GE Healthcare, France) on AKTA avant 80. The molecules were eluted with 25 mM citrate, neutralized and dialysed against PBS, sterilely filtered at 0.2 µm and stored at 4° C. prior usage. The quality of the purified scFv-Fc was assessed by SDS-PAGE, size exclusion chromatography on Superdex 200 (GE Healthcare, France) and the endotoxin level was determined by LAL test.

3. Characterization by Flow Cytometry and Immunohistochemistry 3.1 Flow Cytometry on Magnetic Beads Coated with Atheroma Proteins a/ Protein Extraction The protein extraction was performed as previously described. Briefly, atherosclerotic and healthy proteins were solubilized with a commercially available T-PER lysis buffer (Thermo Fisher Scientific, France) complemented with a protease inhibitors cocktail (Thermo Fischer scientific, France). Solubilization was performed using a Polytron TP-20 Homogenizer 8 (Kinematica, Lucerne, Switzerland). After two centrifugations, at 13,000 g for 45 min at 4° C. to discard insoluble material from the supernatant, the protein concentration of every soluble extract was determined using a Bradford assay kit according to the manufacturer's instructions (Thermo Fisher Scientific, France).

b/ Coupling of Proteins Extracted from Atherosclerotic Rabbit Model to Magnetic Beads Fifty micrograms of proteins extracted from rabbits fed with a high fat diet and developing atheroma plaques, as described previously, were covalently coupled to 300 nm carboxyl-adembeads according to the manufacturer's instructions (Ademtech, France). Three batches of coated protein beads per sample were used for reproducibility. (Deramchia K. et al. Am J Pathol. 2012 June; 180 (6): 2576-89 and Hemadou A. et al. Scientific Reports.)

c/ Flow Cytometry Analysis

Binding of scFv-phages and scFv-Fc fusion antibodies to atherosclerotic rabbit proteins was determined by flow cytometry. Forty microliters of atherosclerotic rabbit proteins coated on beads were added at 5 µg/mL to 100 µL of scFv-phages and scFv-Fc diluted at 10 µg/mL in PBS buffer and incubated for 3 hrs at 4° C. under rotation. A mouse anti-pVIII (Abcam, France) and a rabbit anti human Fcγ specific (Jackson Immunoresearch, USA) primary antibodies were added at 1:1,000 or 1:65 dilutions, respectively, and incubated overnight at 4° C. under rotation. Alexa 488 labeled anti-mouse antibody (Life technologies, France) and Alexa 488 labeled anti-rabbit antibody (Life technologies, France) were used at 1:40 and 1:30 dilutions, respectively for final scFv-phages or scFv-Fc detection.

3.2. Immunohistochemistry on Rabbit, Mouse and Human Sections

ScFv-Fc fusion antibodies were evaluated for binding to paraffin-embedded atheromatous human, mouse and rabbit sections prepared from atheromatous specimens. Each paraffin embedded specimen was deparaffinised and rehydrated. Blocking step ($H_2O_2$ blocking and unspecific site blocking with PBS/1% BSA/0.2% Triton X100) and retrieval step (pH9) were performed. A supplementary blocking of human sections was performed using 5% goat serum followed by addition of goat anti human IgG H+L or Fcγ specific diluted at 100 μg/mL. After washing with PBS/1% BSA, slides were then incubated with scFv-Fc antibodies at 10 μg/mL overnight at 4° C. Specimens were washed with PBS/1% BSA/0.025% Triton X100. Specimens were then incubated with the secondary HRP-conjugated goat anti human (Fcγ specific) antibody (1:1,000) (Jackson Immunoresearch, USA). Negative control slides were only incubated with the secondary antibody.

Figure 2:
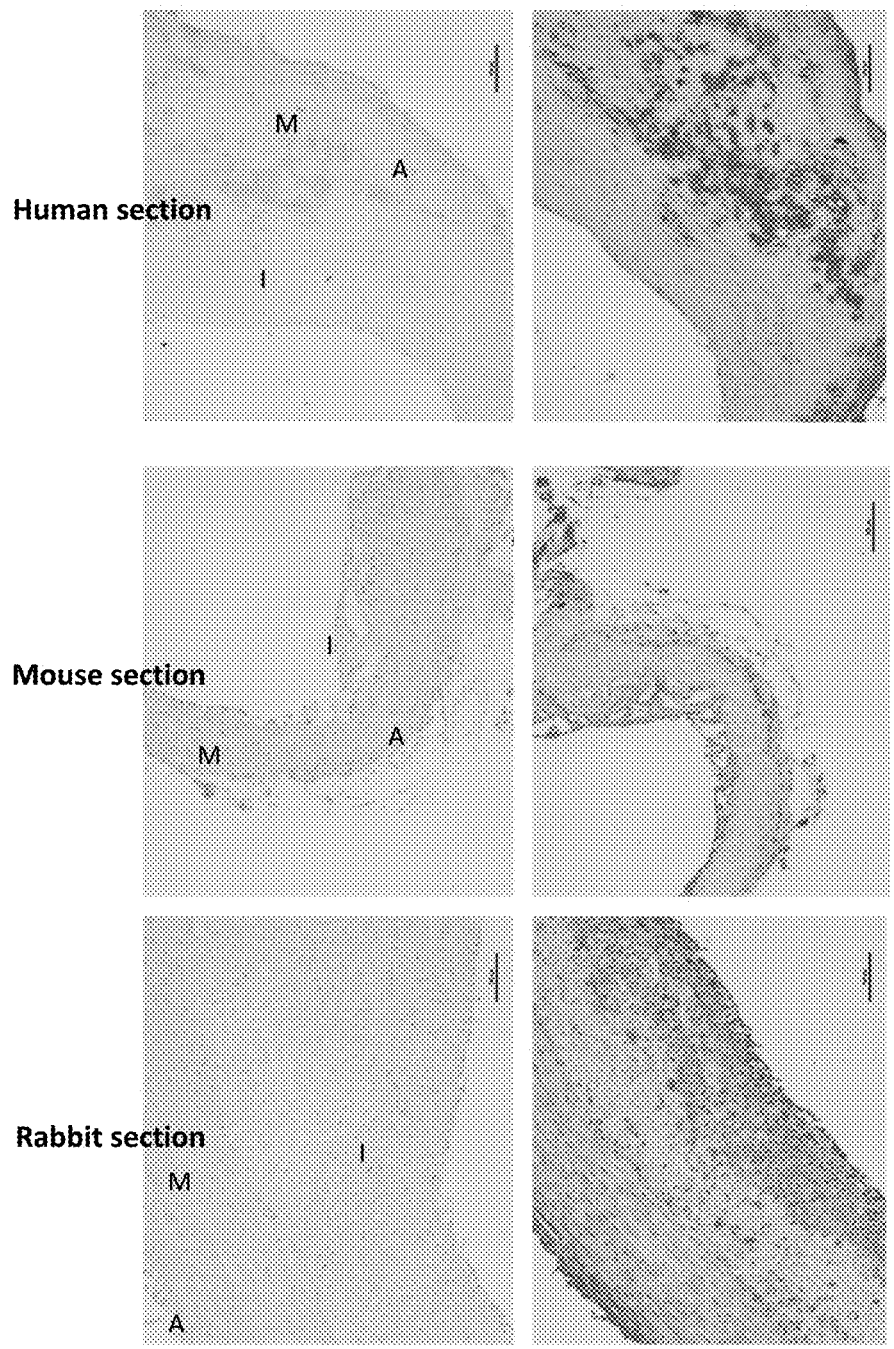
FIG. 2.

The obtained results are presented on FIG. 2.

4. Identification of the Target a—ELISA

ELISA plates were coated with recombinant Galectin3 (Abcam, France), Galectin3BP (Abcam, France) or Galectin3/Galectin3BP complexes at concentration of 5 or 10 μg/mL overnight at 4° C. and were blocked with PBS/5% milk for 1 hour on the following day. Commercially available antibodies or scFv-Fc fusion antibodies were added to respective wells and incubated at room temperature for 2 hrs, followed by Horse Radish Peroxidase (HRP)-conjugated detection antibodies. Commercial antibodies and scFv-Fc fusion antibodies were diluted at 10 μg/mL and 50 μg/mL, respectively.

b—Immunofluorescence Staining

Human tissue specimens were provided by Pr DUCASSE Eric, vascular surgeon at CHU Pellegrin. For immunofluorescence stainings, human sections were deparaffinised and rehydrated. After a retrieval step (pH9), slides were blocked with (1) PBS/1% BSA/0.2% Triton X10 followed by (2) 5% goat serum and (3) addition of goat anti human IgG H+L and Fcγ specific diluted at 100 μg/mL. Primary scFv-Fc produced in baculovirus or commercially available antibodies were added overnight at 4° C. Slides were incubated with scFv-Fc diluted at 50 μg/mL in PBS/1% BSA and, as controls, secondary antibody alone or commercial antibodies according to the manufacturer's instructions. Slides were washed six times for 10 min in PBS/1% BSA/0.025% Triton X100 and the secondary antibody dilutions were applied (Alexa 568 labeled anti-human (1:200) for scFv-Fc or Alexa 488 anti-mouse (1:200) for commercial antibodies). After 1 h incubation, slides were washed in PBS 3 times and mounted with Vectashield (VWR, France). Slides were observed with fluorescent microscope (Nikon, France).

The results show the superposition of binding of the mouse anti-galectin 3 MAbs revealed with an Alexa 488 anti-mouse antibody and the fusion protein of the invention revealed with an Alexa 568 labeled anti-human antibody, highlighting the labeling of the same structures. Results are obtained with a Nikon Fluorescent Microscope.

c—Ex Vivo Fluorescence Imaging

The chest was opened by thoracotomy, the heart exposed and the right atrium cut. A 30-gauge needle was inserted in the left ventricle. PBS-heparin (50 UI/mL; 2.5 mL (Sanofi Aventis, 238 Vitry-sur-Seine, France)) was inoculated followed by 10 mL PBS. Perfusion was continued with 2 mL of PBS containing a formulation of either scFv-Fc P3 antibody or control IgG coupled to fluorochrome Alexa 647 according to the manufacturer's instructions (Alexa 647 antibody labeling kit, Thermofisher Scientific, France). After 20 min, mice were again perfused with 5 mL of 4% v/v paraformaldehyde (PFA). Aorta were then removed and embedded in 80 mm petri dish containing 0.8% p/v high-grade, 245 low melting-point agarose. Aorta were imaged with a Fluorescent Macroscope (Leica Microsystem, France), equipped with a dedicated cube for Alexa 647 acquisition.

Figure 3:
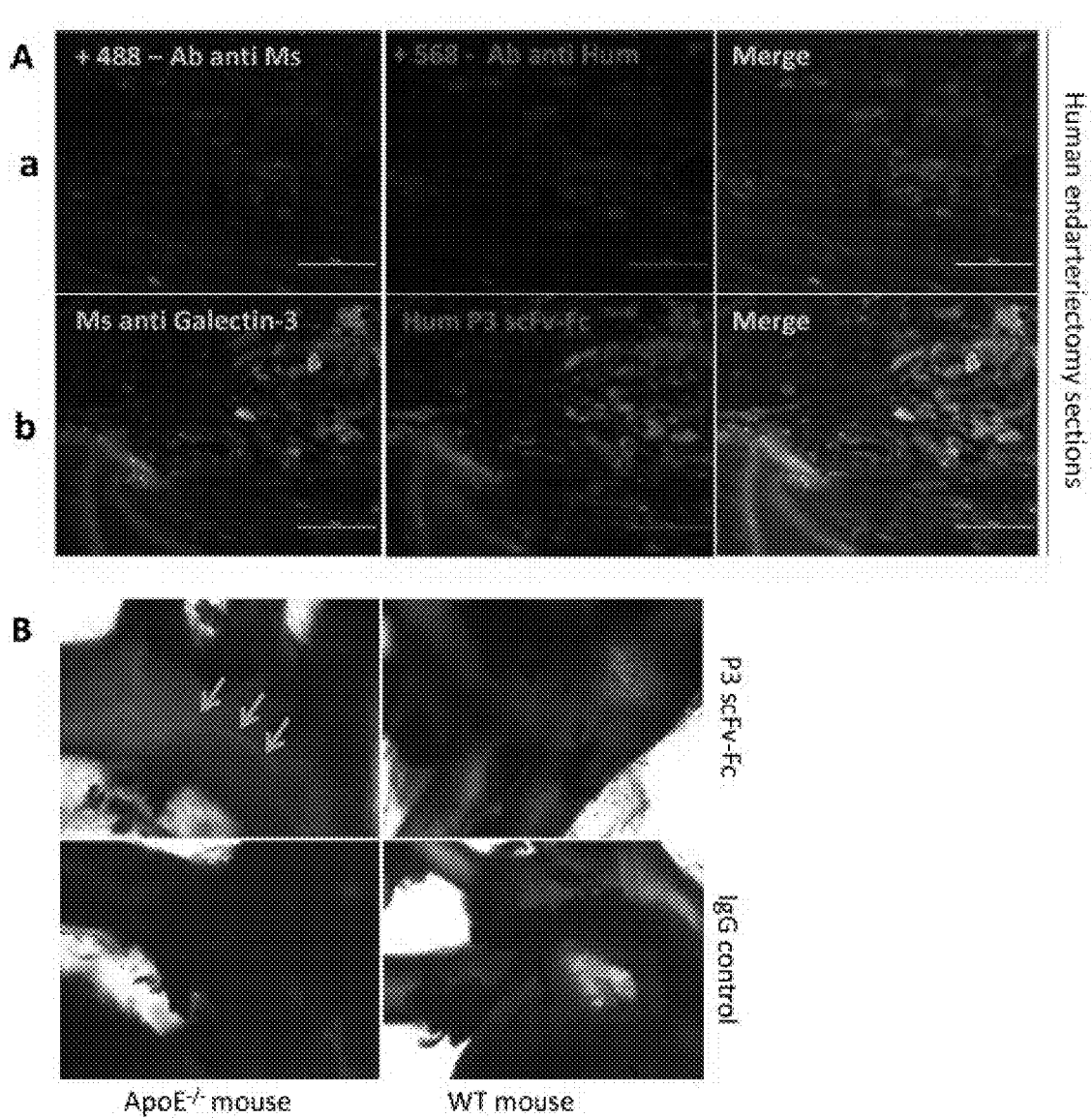
FIG. 3: Immunofluorescent staining of human endarteriectomy sections and aortas of ApoE$^{-/-}$ and WT mouse with P3 scFv-Fc or commercial control antibodies. (A) Double immunofluorescence staining of human endarteriectomy sections. Alexa-fluor 488 anti-mouse antibody (+488-Ab anti Ms) was used to reveal the specific binding of the commercial anti-human Galectin-3 antibody (Ms anti Galectin-3). Alexa-fluor 568 anti-human antibody (+568-Ab anti Human) was used to reveal the specific binding of P3 scFv-Fc (Human P3 scFv-Fc). a) Secondary antibodies alone; (b) Primary antibodies. As seen from co-immunofluorescent staining on human endarteriectomy sections, P3 scFv-Fc and anti-human Gal3 antibody showed overlapping staining. Size bars: 50 μm. (B) Fluorescent macroscopy of P3 scFv-Fc after ex vivo injection in ApoE$^{-/-}$ mouse and WT mouse. A human IgG was used as a negative control antibody. P3 scFv-Fc showed a specific labeling of the atheroma in ApoE–/– mouse.

Results show in FIG. 3 that the detection of atheroma plaques in aorta of atheromatous mouse is evidenced.

Example 3: Preparation of a Specific Binding Protein (IgG1) which Specifically Binds to Galectin-3 Protein 1. Constructions of Bicistronic Vectors Two bicistronic vectors OptiHEK-C3 h/l and OptiHEK-C3 l/h were used for an intermediate production of the nucleotidic sequences of light and heavy chains.

A. Constructions of OptiHEK-C3 h/l

Figure 4A:
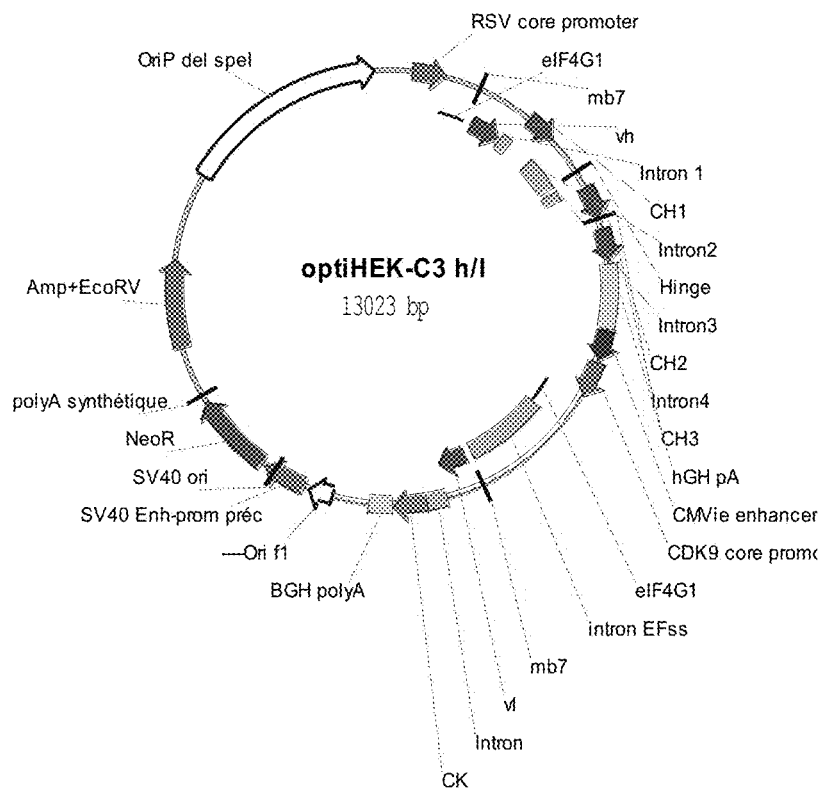
FIG. 4: Restriction card of OptiHEK C3 h/l (FIG. 4A) and OptiHEK C3 l/h vectors (FIG. 4B).
Figure 4B:
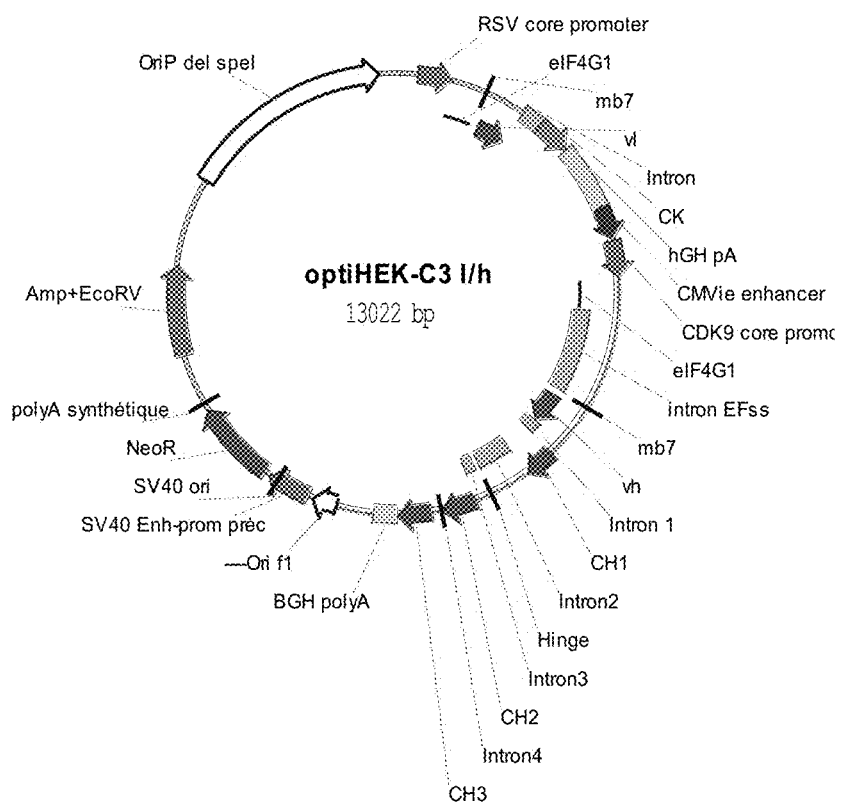

The variable light chain domain and the variable heavy chain domain were isolated from pCEP4 vector (Example 2 section 2) by PCR. The constant light chain (CL, also called CK in FIG. 4) and constant heavy chain CH (CH1, CH2 and CH3) domains are provided under a genomic form with introns. The variable heavy and light chain domains were isolated by PCR, using respectively the primers P1-VH-C3, P2-VH-C3, P1-VL-C3 and P2-VL-C3 as mentioned in table 1. The constant heavy and light chain domains were isolated by PCR, using respectively the primers CH-Int 5', CH-Int 3', CK-Int 5' and CKI-Xbal-5' as mentioned in table 1.

TABLE 1

List of the primers

| | Name Of the primer | Sequences |
|---|---|---|
| For the variable heavy chain domain (VH) | P1-VH-C3 | 5'-CAGAGG AGAGCTAGC GAAGCTTGC CGCCACCAT GCGATGGAG CTGGATCTT CCTGCTGCT GCTGAGCAT CACCAGCGC CAACGCCCA GGTGCAGCT GCAGCAGTC TGGA-3' (SEQ ID No. 27) |
| | P2-VH-C3 | 5'-GCTCGC GGCCGCACT CACCGCTAG ACACGGTCA CGAGGGTGC CCT-3' (SEQ ID No. 28) |
| For the variable light chain domain (VL) | P1-VL-C3 | 5'-TTCCAT TTCAGACTA GTAAGCTTG CCGCCACCA TGCGATGGA GCTGGATCT TCCTGCTGC TGCTGAGCA TCACCAGCG |

TABLE 1 -continued

List of the primers

| Name Of the primer | | Sequences |
|---|---|---|
| | | CCAACGCCG ACATCGTGA TGACCCAGA GC-3' (SEQ ID No. 29) |
| | P2-VL-C3 | 5'-GCCGCA AAGTGCACT TACGCTTGA TTTCCAGCT TGGTGCC G-3' (SEQ ID No.30) |
| For the constant heavy chain domain (CH) | CH-Int 5' | 5'-GTGAGT GCGGCCGCG AGC-3' (SEQ ID No. 31) |
| | CH-Int 3' | 5'-GATCCT CGGCGCGCC TCATCATTT ACCCGG-3' (SEQ ID No. 32) |
| For the constant light chain domain (CL) | CK-Int 5' | 5'-GTAAGT GCACTTTGC GGCCG-3' (SEQ ID No. 33) |
| | CKI-XbaI-5' | 5'-ATCAGC GAGCTCTAG ACTATCAAC ACTCTCCCC TGTTGAAGC T-3' (SEQ ID No. 34) |

Briefly the expression vector OptiHEK-bicistronic was digested by the restriction enzymes NheI and AscI and purified on gel by using NucleoSpin Extract II kit (Macherey-Nagel).

Variable heavy chain domain (VH) and constant heavy chain domain (CH) fragments were then subcloned by recombination using Infusion kit (Ozyme) in between NheI and AscI restriction sites of the OptiHEK-V4 vector to obtain the intermediate vector OptiHEK-C3-h. The intermediate vector OptiHEK-C3-h was then transformed into *E. coli* bacterial cells. The *E. coli* colonies were screened to identify those having the compliant OptiHEK-C3-h vector including the insert VH and CH. Compliant OptiHEK-C3-h vector was then digested by the restriction enzymes SpeI and XbaI and purified on gel by using NucleoSpin Extract II kit. Variable light chain domain (VL) and constant light chain domain (CL) fragments were then subcloned by recombination using Infusion kit in between SpeI and XbaI restriction sites of the OptiHEK-C3-h vector, to obtain the OptiHEK-C3-h/1 vector. OptiHEK-C3-h/1 vector was then transformed into *E. coli* bacterial cells. The *E. coli* colonies were screened to identify those having the compliant OptiHEK-C3-h/1 vector (See FIG. 4A).

B. Constructions of OptiHEK-C3 l/h

Figure 5:
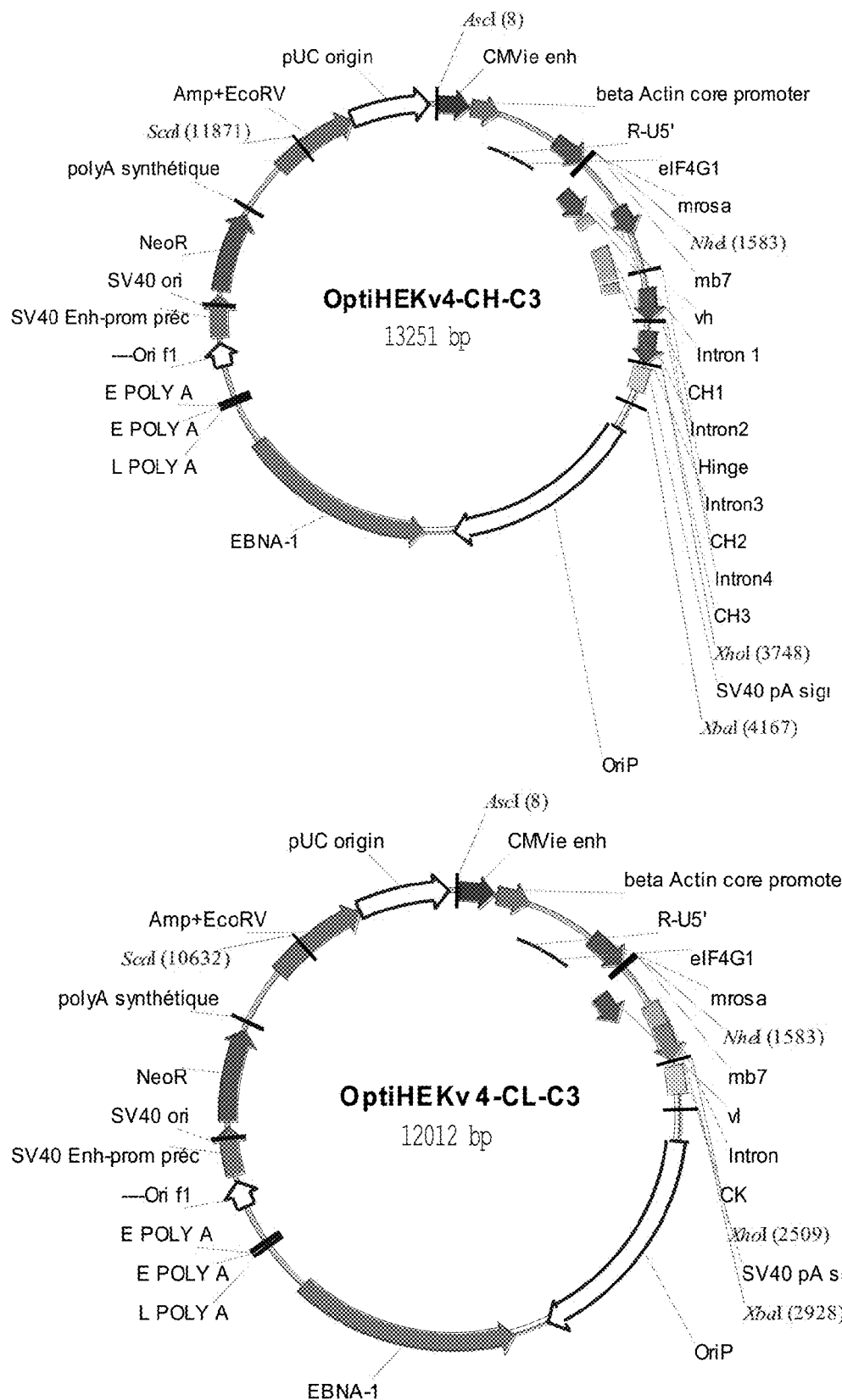
FIG. 5: Restriction card of OptiHEKV4-CH-C3 and OptiHEKV4-CL-C3 vectors.

The variable light chain domain and the variable heavy chain domain were isolated from pCEP4 vector (Example 2 section 2) by PCR, The constant light chain (CL, also called CK in FIG. 5) and constant heavy chain CH (CH1, CH2 and CH3) domains are provided under a genomic form with introns. The variable heavy and light chain domains were isolated by PCR, using respectively the primers P1-VH-C3-2, P2-VH-C3, P1-VL-C3-2 and P2-VL-C3-2 as mentioned in table 2. The constant heavy and light chains domains were isolated by PCR, using respectively the primers CH-Int 5', CH-Int 3', CK-Int 5' and CKI-XbaI-5' as mentioned in table 2.

TABLE 2

List of the primers

| Name Of the primer | | Sequences |
|---|---|---|
| For the variable light chain domain (VL) | P1-VL-C3-2 | 5'-CAGAGGA GAGCTAGCAA GCTTGCCGCC ACCATGCGAT GGAGCTGGAT CTTCCTGCTG CTGCTGAGCA TCACCAGCGC CAACGCCGAC ATCGTGATGA CCCAGAGC-3' (SEQ ID No. 35) |
| | P2-VL-C3-2 | 5'-GCCGCAA AGTGCACTTA CGCTTGATTT CCAGCTTGGT GCCG -3' (SEQ ID No. 36) |
| For the variable heavy chain domain (VH) | P1-VH-C3-2 | 5'-CCATTTC AGACTAGTGA AGCTTGCCGC CACCATGCGA TGGAGCTGGA TCTTCCTGCT GCTGCTGAGC ATCACCAGCG CCAACGCCCA GGTGCAGCTG CAGCAGTCTG GA -3' (SEQ ID No. 37) |
| | P2-VH-C3 | 5'-GCTCGCG GCCGCACTCA CGCTAGACAC GGTCACGAGG GTGCCCT-3' (SEQ ID No. 38) |
| For the constant heavy chain domain (CH) | CH-Int 5' | 5'-GTGAGT GCGGCCGCG AGC -3' (SEQ ID No.31) |
| | 3'CH-xba | 5'-AGGCTGA TCAGCGAGCT CTAGATCATC ATTTACCCGG AGACAGGG A-3' (SEQ ID No. 39) |
| For the constant light chain | CK-Int 5' | 5'-GTAAGTG CACTTTGCG GCCG-3' (SEQ ID |

TABLE 2-continued

List of the primers

| Name Of the primer | | Sequences |
|---|---|---|
| domain (CL) | 3'CK-asc | No. 33)<br>5'-GATCCT<br>CGGCGCGCC<br>CTATCAACA<br>CTCTCCCCT<br>GTTGAAGC<br>T-3'<br>(SEQ ID<br>No. 40) |

Briefly the expression vector OptiHEK-bicistronic was digested by the restriction enzymes NheI and AscI and purified on gel by using NucleoSpin Extract II kit (Macherey-Nagel). Variable light chain domain (VL) and constant light chain domain (CL) fragments were then subcloned by recombination using Infusion kit (Ozyme) in between NheI and AscI restriction sites of the OptiHEK-V4 vector to obtain the intermediate vector OptiHEK-C3-l. The intermediate vector OptiHEK-C3-l was then transformed into E. coli bacterial cells. The E. coli colonies were screened to identify those having the compliant OptiHEK-C3-l including the insert VL and CL. Compliant OptiHEK-C3-l vector was then digested by the restriction enzymes NheI and AscI and purified on gel by using NucleoSpin Extract II kit (Macherey-Nagel). Variable heavy chain domain (VH) and constant heavy chain domain (CH) fragments were then subcloned by recombination using Infusion kit in between SpeI and XbaI restriction sites of the OptiHEK-C3-l vector, to obtain the OptiHEK-C3-l/h vector. OptiHEK-C3-l/h vector was then transformed into E. coli bacterial cells. The E. coli colonies were screened to identify those having the compliant OptiHEK-C3-l/h vector (See FIG. 4B).

2. Constructions of Monocistronic Vector

The light and heavy chains are amplified by PCR from the bicistronic vector as mentioned above, by using the following primers:

TABLE 3

List of the primers

| | Name of the primer | Sequences |
|---|---|---|
| For the full length heavy chain | P1-MB7-V4 | 5'- TTTCC<br>TCTCCTGAC<br>AGCTAGCGA<br>AGCTTGCCG<br>CCACCATGC<br>GATGGAGCT<br>GGATCTTCC<br>T -3'<br>(SEQ ID<br>No. 41) |
| | P2-WT-HI | 5'- CTTGCC<br>GGCCTCGAG<br>TCATCATTT<br>ACCCGGAGA<br>CAGGGA- 3'<br>(SEQ ID<br>No. 42) |
| For the full length | P1-MB7-V4 | 5'- TTTCC<br>TCTCCTGAC<br>AGCTAGCGA |

TABLE 3 -continued

List of the primers

| | Name of the primer | Sequences |
|---|---|---|
| light chain | | AGCTTGCCG<br>CCACCATGC<br>GATGGAGCT<br>GGATCTTCC<br>T -3'<br>(SEQ ID<br>No. 41) |
| | P2-WT-KI | 5'-CTTGC<br>CGGCCTCG<br>AGCTATCA<br>ACACTCTC<br>CCCTGTTG<br>AAGCT-3'<br>(SEQ ID<br>No. 43) |

Briefly, the expression vector OptiHEKV4 was digested by the restriction enzymes NheI and XhoI and purified on gel by using NucleoSpin Extract II kit (Macherey-Nagel). The PCR fragments were then subcloned by recombination using Infusion kit in between NheI and XhoI restriction sites of the OptiHEKV4 vector (See FIG. 5). The monocistronic vectors previously obtained OptiHEKv4-CL-C3 and OptiHEKv4-CH-C3 were then transformed into E. coli bacterial cells. The E. coli colonies were screened by PCR.

3. Expression of the Immunoglobulin IgG1

HEK FreeStyle cells were transfected with indicated LC (OptiHEKv4-CL-C3) and HC (OptiHEKv4-CH-C3) plasmids encoding the heavy chains and light chains according to the supplier instruction with PEI 250 kDa (Sigma-Aldrich) in a 1/4 ratio (DNA/transfection reagent). After 7 days of production at 37° C. 8% $CO_2$, in F17 medium supplemented with 8 mM Glutamine, the supernatant was harvested, clarified by centrifugation and sterilely filtered at 0.2 µm prior to dosage by ELISA using FastELISA kit (RD Biotech, France) for human IgG. When IgG1 were used as purified molecules, this was performed by a one-step affinity chromatography with HiTrapp FF, protein A (GE Healthcare, France) on AKTA avant 80. The IgG1 molecules were eluted with 25 mM citrate and dialysed against PBS, sterilely filtered at 0.2 µm and stored at 4° C. prior usage. The quality of the purified IgG1 was assessed by SDS-PAGE, size exclusion chromatography on Superdex 200 (GE Healthcare, France) and the endotoxin level was determined by LAL test.

4. Immunohistochemistry on Mouse and Human Sections.

IgG1 molecules were evaluated for binding to paraffin-embedded atheromatous human sections obtained from human biopsies from two different donor and mouse sections prepared from murine animal model. Each paraffin embedded specimen was deparaffinised and rehydrated. Blocking step ($H_2O_2$ blocking and unspecific site blocking with PBS/1% BSA/0.2% Triton X100) and retrieval step (pH9) were performed. A supplementary blocking of human sections was performed using 5% goat serum followed by addition of goat anti human IgG H+L or Fcγ specific diluted at 100 µg/mL. After washing with PBS/1% BSA, slides were then incubated with scFv-Fc antibodies at 10 µg/mL overnight at 4° C. Specimens were washed with PBS/1% BSA/0.025% Triton X100. Specimens were then incubated with the secondary HRP-conjugated goat anti human (Fcγ specific) antibody (1:1,000) (Jackson Immunoresearch, USA). Negative control slides were only incubated with the secondary antibody.

Figure 6:
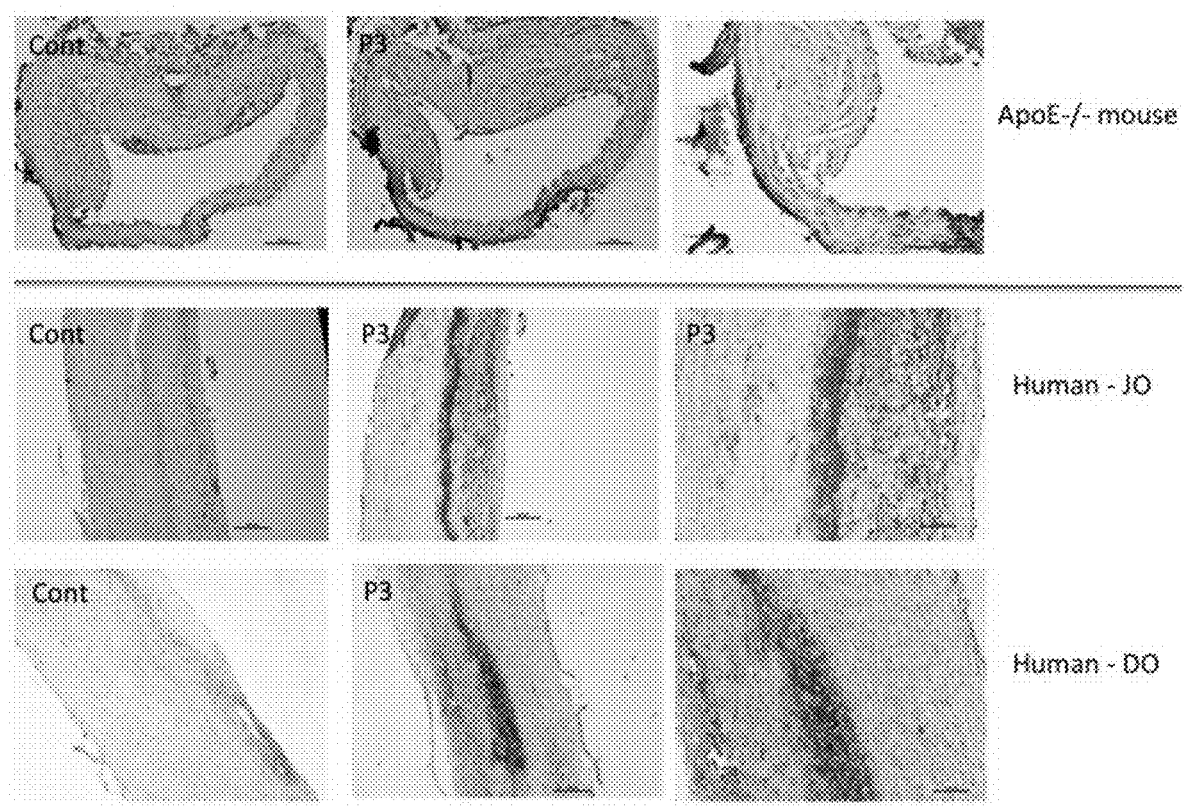
FIG. 6.

The obtained results are presented on FIG. 6.

The IgG molecule is able to stain structures in mouse and human atheroma.

Example 4: MRI Imaging on APOE−/− Mice Using scFv-Fc-2C P3 Antibody Crafted on Nanoparticles Containing Iron-Oxide The Bio-functionalization of the nanoparticle (SPIO-NE which is a nanoemulsion containing iron oxide nanoparticles (SPIO) for MRI imaging) with scFv-Fc-2C P3 antibody (as produced in Example 2.1) was performed using a Maleimide-Based Protein Conjugation. First, the two cysteines of 100 µg of the human antibody (1 mg·mL$^{-1}$) were activated for 45 min with 18 µL TCEP solution at 1 mM (molar ratio TCEP/P3 equal to 20) at 4° C. Then the nanoemulsion was incubated with the activated antibody at 4° C. overnight. After the functionalization, non-grafted antibodies were removed from the nanoemulsion thanks to the superparamagnetic properties of the NE using magnetic sorting. The functionalization was performed in HEPES buffer 10 mM 0.5 mM EDTA pH 7.

The accumulation of the targeted contrast agent was visualized by the estimation of R2* maps segmented at the plaque level and estimated from a multi-gradient-echo sequence measured with a horizontal 4.7 T Biospec system (Bruker, Ettlingen, Germany).

Multi slice MGE sequences: repetition time TR≈1,000±100 ms, first echo time TE=3.5 ms, ΔTE=4.5 ms, 15 echoes, α=60°, NEx=4, resolution=0.1×0.1×1 mm. R2* maps were extracted from the fit of the MR signal (S) using the following equation: $S=S_0 e^{-TE \cdot R_2^*} \times |\text{sinc}(\gamma \cdot (\Delta B_0/dz)/2 \cdot TE))|$, where S0 is the signal when TE approaches 0 ms.

A map of the local gradient field (ΔB0/dz) as well as the R2* maps were estimated as proposed by Dahnke et al. An increase in the mean R2* value was observed 24 h after injection of the targeted nanoparticle, highlighting its in vivo accumulation in the atheroma plaque thanks to the human antibody grafted on the MRI nanoparticle.

Figure 7:
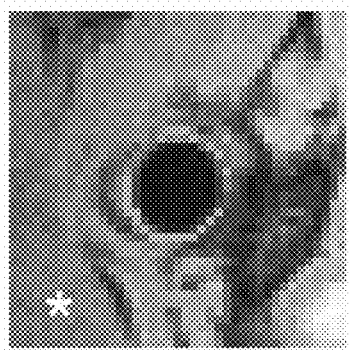
FIG. 7.
Figure 7:
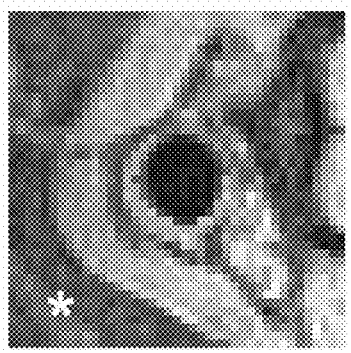
Figure 7:
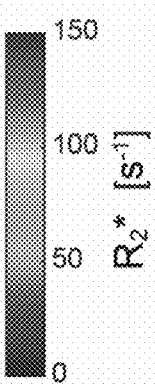
Figure 7:
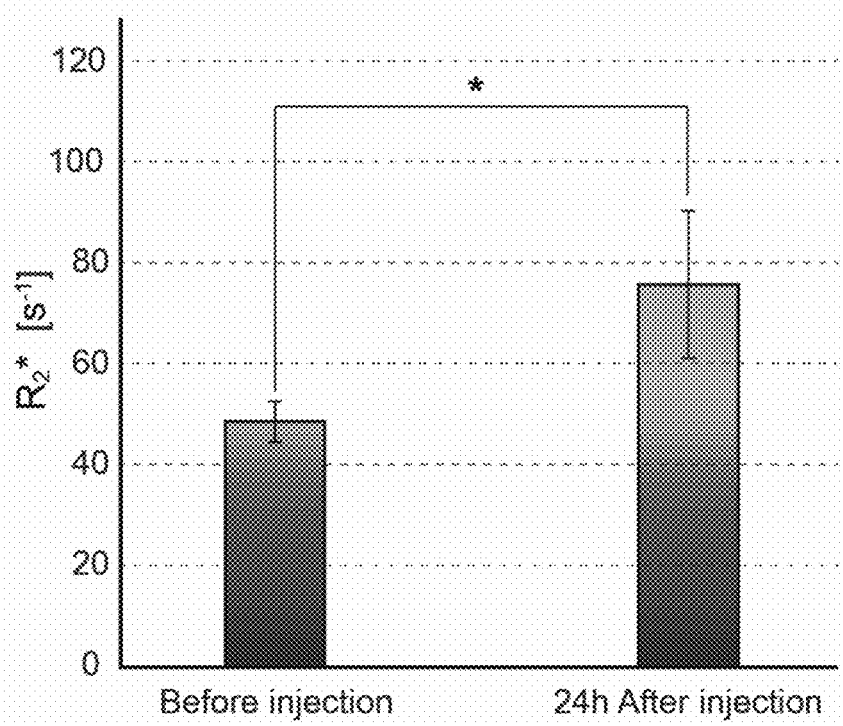

The obtained results are presented on FIG. 7.

The invention claimed is:

1. A specific binding molecule which specifically binds to galectin-3 protein, said specific binding molecule comprising: a variable heavy domain (VH) comprising an amino acid sequence having at least 90% identity to SEQ ID No. 1, wherein said amino acid sequence comprises CDR1, CDR2 and CDR3 regions consisting of SEQ ID No. 3, SEQ ID No. 4 and SEQ ID No. 5, and a variable light domain (VL) comprising an amino acid sequence having at least 90% identity to SEQ ID No. 2, wherein said amino acid sequence comprises CDR1, CDR2 and CDR3 regions consisting of SEQ ID No. 6, SEQ ID No. 7 and SEQ ID No. 8.

2. A specific binding molecule which specifically binds to galectin-3 protein, said specific binding molecule comprising: a variable heavy domain (VH) comprising the amino acid sequence of SEQ ID No. 1; and a variable light domain (VL) comprising the amino acid sequence of SEQ ID No. 2.

3. A specific binding molecule which specifically binds to galectin-3 protein, said specific binding molecule being an antibody or a fragment thereof, comprising: the variable heavy domain (VH) of SEQ ID No. 1, comprising CDR1, CDR2 and CDR3 regions consisting of SEQ ID No. 3, SEQ ID No. 4 and SEQ ID No. 5, and the variable light domain (VL) of SEQ ID No. 2, comprising CDR1, CDR2 and CDR3 regions consisting of SEQ ID No. 6, SEQ ID No. 7 and SEQ ID No. 8.

4. The specific binding molecule according to claim 1, wherein the specific binding molecule is an antibody or fragment thereof.

5. The specific binding molecule according to claim 4, wherein the antibody is a monoclonal antibody.

6. The specific binding molecule according to claim 4, wherein the fragment is a Fab, F(ab') or Fv fragment or a scFv molecule.

7. The specific binding molecule according to claim 1, comprising an amino acid sequence having at least 85% identity to SEQ ID No. 10.

8. A pharmaceutical composition comprising a therapeutically effective amount of the specific binding molecule according to claim 1 as an active substance and at least one pharmaceutically acceptable carrier.

9. A fusion protein comprising the specific binding molecule according to claim 1 and a human immunoglobulin G (IgG) Fc fragment.

10. A diagnostic composition comprising the specific binding molecule according to claim 1 as a diagnostic agent and a carrier.

11. A diagnostic kit for the detection of galectin-3 protein, comprising the specific binding molecule according to claim 1.

12. A nucleic acid sequence encoding the specific binding molecule according to claim 1.

13. A nucleic acid sequence encoding the specific binding molecule according to claim 1, comprising at least 85% identity to the nucleic acid sequence SEQ ID No. 11.

14. A nucleic acid sequence encoding the specific binding molecule according to claim 1, having the nucleic acid sequence SEQ ID No. 11.

15. A vector comprising the nucleic acid sequence of claim 12.

16. A host cell comprising the vector of claim 15.

17. A method for the treatment of atherosclerosis by administering the specific binding molecule of claim 1.

* * * * *